(12) United States Patent
Arnould et al.

(10) Patent No.: US 7,030,123 B2
(45) Date of Patent: Apr. 18, 2006

(54) INDOLE DERIVATIVES WITH VASCULAR DAMAGING ACTIVITY

(75) Inventors: Jean-Claude Arnould, Reims Cedex (FR); Thomas Geoffrey Bird, Reims Cedex (FR); Francis Thomas Boyle, Macclesfield (GB); David Charles Blakey, Macclesfield (GB)

(73) Assignee: AstraZeneca AB, Södertälje (SE)

( * ) Notice: Subject to any disclaimer, the term of this patent is extended or adjusted under 35 U.S.C. 154(b) by 79 days.

(21) Appl. No.: 10/276,347

(22) PCT Filed: May 25, 2001

(86) PCT No.: PCT/GB01/02335

§ 371 (c)(1),
(2), (4) Date: Nov. 13, 2002

(87) PCT Pub. No.: WO01/92224

PCT Pub. Date: Dec. 6, 2001

(65) Prior Publication Data

US 2003/0216356 A1  Nov. 20, 2003

(30) Foreign Application Priority Data

May 31, 2000 (EP) ............................................. 00401551
Oct. 25, 2000 (EP) ............................................. 00402956

(51) Int. Cl.
*A61K 31/404* (2006.01)
*A61K 31/496* (2006.01)
*C07D 209/40* (2006.01)
*C07D 403/12* (2006.01)

(52) U.S. Cl. .................. 514/254.09; 514/415; 544/373; 548/414; 548/483

(58) Field of Classification Search ............ 514/254.09, 514/415, 418, 419; 548/414, 483; 544/373
See application file for complete search history.

(56) References Cited

U.S. PATENT DOCUMENTS

| 3,901,914 A | 8/1975 | Hannah |
| 4,533,672 A | 8/1985 | Eakin et al. |
| 4,952,584 A | 8/1990 | Thompson et al. |
| 6,147,085 A | 11/2000 | Horvath et al. |

FOREIGN PATENT DOCUMENTS

| EP | 0 372 962 A2 | 6/1990 |
| EP | 0 393 575 B1 | 10/1990 |
| JP | 2000-80295 A | 3/2000 |
| WO | WO 98/39323 | 9/1998 |
| WO | WO 99/29660 | 6/1999 |
| WO | WO 99/29661 | 6/1999 |
| WO | WO 99/51598 | 10/1999 |
| WO | WO 99/51600 | 10/1999 |
| WO | WO 00/48606 | 8/2000 |
| WO | WO 00/66585 | 11/2000 |
| WO | WO 01/19794 A2 | 3/2001 |
| WO | WO 01/22954 A2 | 4/2001 |
| WO | WO 01/29025 A2 | 4/2001 |
| WO | WO 01/82909 A2 | 11/2001 |

OTHER PUBLICATIONS

Aleksandrzak, et al. Antimitotic Activity of Diaryl Compounds With Structural Features Resembling Combretastatin A–4. Anti–Cancer Drugs, 9, 545–550 (1998).

McGown, et al. Structural and Biochemical Comparison of the Anti–Mitotic Agents Colchicine, Combretastatin A4 and Amphethinile. Anti–Cancer Drug Design, 3, 249–254 (1989).

Galbraith, et al. Effects of Combretastatin A4 Phosphate on Endothelial Cell Morphology in Vitro and Relationship to Tumour Vascular Targeting Activity in Vivo. Anticancer Research, 21, 93–102 (2001).

Bolton, et al. Synthesis and Potential Anxiolytic Activity of 4–Amino–Pyrido[2,3–b]Indoles. Bioorganic & Medicinal Chemistry Letters, 3(10), 1941–1946 (1993).

Blackburn, et al. (+)11–Amino–2,6–Dimethyl–1,2,3, 4–Tetrahydro–6H–Quinindolin–1–One, a Novel GabaA Modulator with Potential Anxiolytic Activity. Bioorganic & Medicinal Chemistry Letters, 4(2), 279–284 (1994).

McGown, et al. Pre–Clinical Studies of a Novel Anti–Mitotic Agent, Amphethinile. Br. J. Cancer, 57, 157–159 (1988).

McGown, et al. Interaction of the Novel Agent Amphethinile with Tubulin. Br. J. Cancer, 59, 865–868 (1989).

Newell, et al. Evaluation of Rodent–Only Toxicology for Early Clinical Trials with Novel Cancer Therapeutics. British Journal of Cancer, 81(5), 760–768 (1999).

Dark, et al. Combretastatin A–4, an Agent That Displays Potent and Selective Toxicity Toward Tumor Vasculature. Cancer Research, 57, 1829–1834 (1997).

(Continued)

Primary Examiner—Joseph K. McKane
Assistant Examiner—Rebecca Anderson

(57) ABSTRACT

The invention provides a compound of Formula (I).

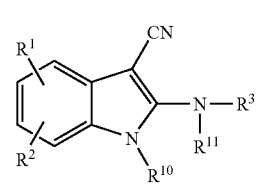

Formula (I)

Wherein R1, R2, R3, R10 and R11 have the meanings given in the description. Such compounds are predicted to cause the selective destruction of tumour vasculature. They may therefore be used to inhibit and/or reverse, and/or alleviate symptoms of angiogenesis and/or any disease state associated with angiogenesis.

10 Claims, No Drawings

OTHER PUBLICATIONS

Player, et al. Synthesis of 1,3–Disubstituted–2–amino–5–hydroxyindoles by Reductive Aromatization. J. Heterocyclic Chem., 30, 125–128 (1993).

Hess, et al. 7–Deazaadenines Bearing Polar Substituents: Structure–Activity Relationships of New A1 and A3 Adenosine Receptor Antagonists. J. Med. Chem., 43, 4636–4646 (2000).

Fuse, et al. Application of Pharmacokinetically Guided Dose Escalation With Respect to Cell Cycle Phase Specificity. Journal of the National Cancer Institute, 86(13), 989–996 (1994).

Portnov, et al. Khim Gereotsikl Soedin, 3, 400–402 (1991).

Eger, et al. Synthesis of Substituted Indoles and Pyrimido [4,5–b]indoles by Dehydrogenation of Tetrahydroindoles and Tetrahydropyrimidoindoles. Liebigs Ann. Chem., 465–470 (1993).

INDOLE DERIVATIVES WITH VASCULAR DAMAGING ACTIVITY

This application is a national stage filing under 35 U.S.C. 371 of PCT application PCT/GB01/02335, filed May 25, 2001, which claims priority from European Patent Application Nos. 00401551.7, filed May 31, 2000, and 00402956.7, filed Oct. 25, 2000, the specifications of all of which are incorporated by reference herein. PCT Application PCT/GB01/02335 was published under PCT Article 21(2) in English.

This invention relates to vascular damaging agents and their uses. In particular it relates to certain novel compounds which may be of use as vascular damaging agents, to methods for preparing the compounds, to their use as medicaments (including in methods for the treatment of angiogenesis or disease states associated with angiogenesis) and to pharmaceutical compositions containing them. The invention also relates to the use of such compounds, and of certain analogous, known compounds in the manufacture of medicaments for the production of anti-angiogenic and/or anti-vascular effects.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma, Kaposi's sarcoma and haemangioma (Fan et al, 1995, *Trends Pharmacol. Sci.* 16: 57–66; Folkman, 1995, *Nature Medicine* 1: 27–31). Formation of new vasculature by angiogenesis is a key pathological feature of several diseases (J. Folkman, *New England Journal of Medicine* 333, 1757–1763, 1995). For example, for a solid tumour to grow it must develop its own blood supply upon which it depends critically for the provision of oxygen and nutrients; if this blood supply is mechanically shut off the tumour undergoes necrotic death. Neovascularisation is also a clinical feature of skin lesions in psoriasis, of the invasive pannus in the joints of rheumatoid arthritis patients and of atherosclerotic plaques. Retinal neovascularisation is pathological in macular degeneration and in diabetic retinopathy.

Reversal of neovascularisation by damaging the newly-formed vascular endothelium is therefore expected to have a beneficial therapeutic effect.

The present invention is based on the discovery of compounds that show surprising activity in in vitro cell detachment assays, in particular by inducing changes in the shape of proliferating endothelial cells and by causing rapid cell detachment, which activity is a likely indicator of vascular damaging activity. The compounds are expected to cause damage to newly formed vasculature, for example the vasculature of tumours, without affecting the normal, established vascular endothelium of the host species. This vascular damage would effectively reverse the process of angiogenesis, as compared to known anti-angiogenic agents which can prevent vasculature formation but which tend to be less effective once the vasculature has formed.

Such vascular-damaging activity would clearly be of value in the treatment of disease states associated with angiogenesis such as cancer, diabetes, psoriasis, rheumatoid arthritis, Kaposi's sarcoma, haemangioma, acute and chronic nephropathies, atheroma, arterial restenosis, autoimmune diseases, acute inflammation, endometriosis, dysfunctional uterine bleeding and ocular diseases with retinal vessel proliferation.

A compound of Formula (I) in which $R^1$ is Ph—S— and both $R^2$ and $R^3$ are H (2-amino-3-cyano-5-(phenylthio) indole, also known as amphethinile) is disclosed in U.S. Pat. No. 4,533,672 as an anti-cancer agent, as is a compound of Formula (I) in which $R^1$ is Ph—S—, $R^2$ is H and $R^3$ is —C(O)—O—$CH_2CH_3$ (ethyl 3-cyano-5-(phenylthio)indol-2-ylcarbamate). However, anti-cancer activity, in this case an apparent inhibition of tumour growth in mice, is not in itself an indicator of vascular damaging activity, for which the compounds of the present invention are of interest. Amphethinile has also been disclosed as a tubulin-binding agent (McGowan and Fox, *British Journal of Cancer* 59, 865–868, 1989).

Several anticancer agents have been described which bind to tubulin, these include Taxol™ and Taxotere™. However, these agents do not act as selective vascular targeting agents. For example, Taxol does not cause cell detachment in the HUVEC detachment assay, described herein. Other tubulin-binding agents such as colchicine and vinca alkaloids such as vincristine only elicit vascular damaging activity at doses approaching the maximum tolerated dose (MTD) (see Dark et al 1997 *Cancer Research* 57, 1829–1834). More recently Combretastatin A4 has been described which is a tubulin binding agent which acts as a selective vascular targeting agent, producing anti-vascular effects at doses greater than 10-times less than the MTD (Dark et al 1997 *Cancer Research* 57, 1829–1834). Thus, tubulin-binding activity is not in itself an indicator of compounds that have selective vascular damaging activity.

Tubulin binding agents that do cause selective destruction of tumour vasculature such as combretastatin and ZD6126 (N-acetylcolchinol phosphate) have been reported in vitro at non-cytotoxic concentrations to cause selective effects on the cell shape of proliferating endothelial cells leading to endothelial cell detachment[Dark et al, *Cancer Research* 57, 1829–34, 1997; Galbraith et al, 21(1A), 93–102, 2001; Blakey D C et al, *Proceedings of the American Association for Cancer Research,* 41, 329, 2000 abstract 2086, Davis P D et al, *Proceedings of the American Association for Cancer Research,* 41, 329, 2000 abstract 2085; Chaplin D J & Dougherty G J, *Br J Cancer,* 80, Suppl 1, 57–64, 1999].

The compounds of the present in invention are tubulin binding agents that have similar activity to combretastatin and ZD6126 on proliferating endothelial cells. It can therefore be expected that the compounds of the present invention will have damaging effects on newly-formed vasculature, for example the vasculature of tumours. It can reasonably be predicted, for example, that they will be capable of causing selective destruction of tumour vasculature, both in vitro and in vivo. Destruction of tumour vasculature in turn leads to a reduction in tumour blood flow and to tumour cell death due to starvation of oxygen and nutrients, ie, to anti-tumour activity [Davis P D et al; Chaplin D J & Dougherty G J; Blakey D C et al, all supra].

Thus, according to the first aspect of the invention there is provided a compound of Formula (I):

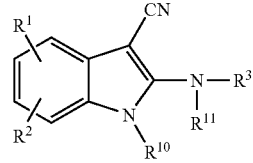

Formula (I)

wherein $R^1$ and $R^2$ are independently selected from hydrogen, halogen, —CN, a hydrocarbyl group or a group of Formula (II):

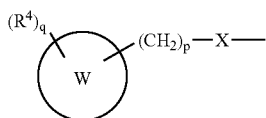

Formula (II)

wherein W is aryl or a heterocyclic group, $R^4$ is independently selected from hydrogen, halogen, —OH, amino, alkanoylamino, —OPO₃H₂, or a hydrocarbyl group, wherein the amino group is optionally substituted by an amino acid residue and the hydroxy group is optionally esterified or two $R^4$ groups together form an optionally substituted cyclic or heterocyclic group;

X is selected from —S—, —O—, —S(O)—, —S(O₂)— and —NH—;

p is an integer from 0 to 4; and q is an integer from 1 to 4;

$R^3$ and $R^{10}$ are independently selected from hydrogen, lower alkyl or a group of Formula (IV):

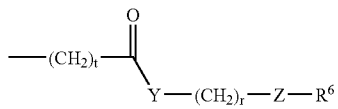

Formula (IV)

wherein Y is selected from —NH—, —O— or a bond;

Z is selected from —NH—, —O—, —C(O)— or a bond;

r is an integer from 0 to 4;

t is an integer from 0 to 1;

$R^6$ is hydrogen, a hydrocarbyl group or a group of Formula (V):

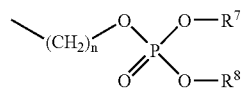

Formula (V)

wherein n is an integer of from 1 to 6, and;

$R^7$ and $R^8$ are independently selected from hydrogen or a hydrocarbyl group; and $R^{11}$ is hydrogen or lower alkyl;

or a salt or solvate thereof;

provided that:

i) when $R^1$ is an unsubstituted phenylthio group (Ph—S—), $R^2$ is H, $R^{10}$ is H and $R^{11}$ is H then $R^3$ is neither H nor —C(O)—O—CH₂CH₃; and ii) $R^1$, $R^2$ and $R^3$ are not all hydrogen.

Whilst pharmaceutically acceptable salts of compounds of the invention are preferred, other non-pharmaceutically acceptable salts of the invention may be useful in the preparation of pharmaceutically-acceptable salts of compounds of the invention.

According to a further feature of the first aspect of the present invention there is provided a compound of the general Formula (Ia):

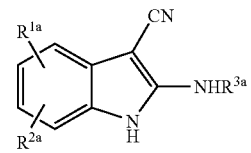

Formula (Ia)

or a derivative thereof, wherein $R^{1a}$ and $R^{2a}$ are independently selected from hydrogen, halogen (such as fluorine, chlorine or bromine), —OH, —CN, a hydrocarbyl group (such as a lower alkyl group) or a group of Formula (IIa):

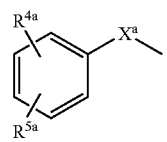

Formula (IIa)

wherein $R^{4a}$ and $R^{5a}$ are independently selected from hydrogen, halogen (such as fluorine, chlorine or bromine), —OH or a hydrocarbyl group (such as a $C_1$–$C_{10}$ alkyl group, an alkoxy group such as —O-alkyl or a group of Formula (IIIa):

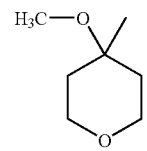

Formula (IIIa)

or a carbonyl group of the Formula —C(O)—$R^{9a}$ where $R^{9a}$ is hydrogen, —OH, a hydrocarbyl group such as a lower alkyl group or an alkoxy group), or $R^{4a}$ and $R^{5a}$ together form a cyclic or heterocyclic group, for instance to make $R^{1a}$ into —X-naphthyl;

$X^a$ is selected from —S—, —O—, —S(O)—, —S(O₂)— and —NH—;

$R^{3a}$ is either hydrogen or a group of Formula (IVa):

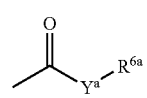

Formula (IVa)

wherein $Y^a$ is selected from —NH—, —O— or a bond; and $R^{6a}$ is hydrogen or a hydrocarbyl group (such as an alkyl, aryl, alkoxy or phenoxy group, preferably —Ph or a lower alkyl group) or a group of Formula (Va):

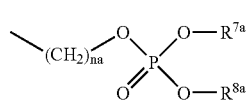

Formula (Va)

wherein na is an integer of from 1 to 6, preferably 2 or 3, and $R^{7a}$ and $R^{8a}$ are independently selected from hydrogen or a hydrocarbyl group (in particular an alkaryl group such as —(CH₂)$_{ma}$—Ph where ma is an integer of from 1 to 6, preferably 1);

provided that:
i) when $R^1$ is an unsubstituted phenylthio group (Ph—S—) and $R^{2a}$ is H, $R^{10a}$ is H and $R^{11a}$ is H then $R^{3a}$ is neither H nor —C(O)—O—CH$_2$CH$_3$; and
ii) $R^{1a}$, $R^{2a}$ and $R^{3a}$ are not all hydrogen.

In this specification, the term "alkyl" refers to straight or branched chain alkyl groups, suitably containing up to 20 and preferably up to 10 or up to 6 carbon atoms, which may be substituted with one or more functional groups. The terms "$C_{1-4}$alkyl" and "$C_{1-6}$alkyl" refer to both straight-chain and branched alkyl groups containing between 1 and 4 carbon atoms and between 1 and 6 carbon atoms respectively. The terms "alkenyl" and "alkynyl" refer to optionally substituted unsaturated straight or branched chains which include for example from 2 to 20 carbon atoms, in particular from 2 to 10 or from 2 to 6 carbon atoms; these chains may include one or more double or triple bonds respectively. The term "alkoxy" refers to alkyl, alkenyl or alkynyl groups containing the group —O—, for example methoxy, ethoxy and propoxy. The term "alkanoyl" refers to alkyl, alkenyl or alkynyl groups containing the group —C(O)—, for example acetyl, propanoyl and butanoyl. The term "alkanoylamino" refers to alkyl, alkenyl or alkynyl groups containing the group —C(O)— followed by —N(H)—, for example acetylamino, propanoylamino and butanoylamino. The term "carbamoyl" refers to the group —C(O)—NH$_2$. The term "carbamoylalkyl" refers to an alkyl chain terminating in a carbamoyl group, for example carbamoylmethyl which has the formula —CH$_2$—C(O)—NH$_2$. The term "halogen" refers to chloro, bromo, fluoro or iodo.

The term "cyclic group" refers to an optionally substituted carbon ring structure, which may contain one or more double or triple bonds, the term encompassing aryl and aralkyl groups.

The term "aryl" refers to wholly or partially aromatic groups such as phenyl (for which the abbreviation "Ph" is used) or naphthyl, which may be substituted with one or more functional groups. The term "alkaryl" means an alkyl group having at least one (optionally substituted) aryl substituent, and the term "aralkyl" an aryl group having at least one (optionally substituted) alkyl substituent.

The term "lower", applied to the terms alkyl, alkenyl, alkynyl, alkoxy, alkanoyl, alkanoylamino, alkaryl and aralkyl, means a group containing from 1 to 6 carbon atoms, preferably from 1 to 4.

The term "hydrocarbyl" refers to any structure comprising carbon and hydrogen atoms. For example, these may be alkyl, alkenyl, alkynyl, alkoxy, aryl such as phenyl or naphthyl, alkaryl, aralkyl, cycloalkyl, cycloalkenyl or cycloalkynyl. Suitably they will contain up to 20 and preferably up to 10 carbon atoms. They may be substituted with other functional groups, or an alkyl chain optionally substituted with other functional groups and they may include heteroatoms such as oxygen, nitrogen, sulphur and/or phosphorous within a carbon chain or ring.

The term "heterocyclic group" includes optionally substituted aromatic, partially aromatic or non-aromatic rings or mixtures thereof, for example containing from 3 to 20, suitably from 5 to 10 ring atoms, at least one of which is a heteroatom such as oxygen, sulphur or nitrogen. Examples of such groups include morpholinyl, morpholino, piperazinyl, piperidino, furyl, thienyl, pyrrolyl, pyrrolidinyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, quinolinyl, iosquinolinyl, quinoxalinyl, benzthiazolyl, benzoxazolyl, benzothienyl or benzofuryl.

The term "functional group" refers to reactive groups such as halogen, cyano, nitro, oxo, C(O)$_y$R$^a$, OR$^a$, S(O)$_z$R$^a$, NR$^b$R$^c$, OC(O)NR$^b$R$^c$, C(O)NR$^b$R$^c$, —NR$^7$C(O)$_y$R$^6$, —NR$^a$CONR$^b$R$^c$, —C=NOR$^a$, —N=CR$^b$R$^c$, S(O)$_z$NR$^b$R$^c$, C(S)$_y$R$^a$, C(S)OR$^a$, C(S)NR$^b$R$^c$ or —NR$^b$S(O)$_z$R$^a$ where R$^a$, R$^b$ and R$^c$ are independently selected from hydrogen or optionally substituted hydrocarbyl, or R$^b$ and R$^c$ together form an optionally substituted ring which optionally contains further heteroatoms such as S(O)$_z$, oxygen and nitrogen. In this paragraph, y is an integer of 1 or 2 and z is 0 or an integer from 1 to 3.

The term "heteroatom" as used herein refers to non-carbon atoms such as oxygen, nitrogen, sulphur or phosphorous atoms. Where nitrogen atoms are present, they will generally be present as part of an amino or amido residue so that they will be substituted for example by hydrogen, alkyl or carbonyl.

The term "derivative" as used herein refers to salts, solvates and pro-drugs of compounds of the invention.

An "amino acid residue" is defined as that derived from the coupling of an L-amino acid with an amino group via an amide bond. This bond can either be formed via a carboxylate group on the amino acid backbone or via a side chain carboxylate group, preferably via a carboxylate group on the amino acid backbone. Amino acid residues include those derived from natural and non-natural amino acids, preferably natural amino acids and include α-amino acid residues β-amino acid residues and γ-amino acid residues. For the avoidance of doubt amino acids include those with the generic structure:

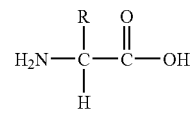

where R is the amino acid side chain. The definition of amino acid also includes amino acid analogues which have additional methylene groups within the amino acid backbone, for example β-alanine and amino acids which are not naturally occurring such as cyclohexylalanine. Preferred amino acid residues are those derived from naturally occurring amino acids. For avoidance of doubt the term 'naturally occurring amino acids' is defined as those amino acids which occur in the proteins of animals.

Preferred amino acids include glycine, alanine, valine, leucine, isoleucine, methionine, proline, phenylalanine, tryptophan, serine, threonine, cysteine, tyrosine, asparaginine, glutamine, aspartic acid, glutamic acid, lysine, arginine, histidine, β-alanine and ornithine. More preferred amino acids include glutamic acid, serine, threonine, arginine, glycine, alanine, β-alanine and lysine. Especially preferred amino acids include glutamic acid, serine, and glycine.

"Esterifying groups at $R_4$" are esterifying groups which increase the solubility of the molecule in water at a pH of approximately pH=7. Such groups include groups with ionisable groups, such as acidic functions or basic functions and groups containing a hydrophilic function. Basic functions include: amino, morpholino, piperidino, piperazinyl, pyrrolidino, amino acids and imidazolino. Acidic functions include: carboxy, sulphonic acid, phosphate, sulphate and acid mimetics such as tetrazolyl. Hydrophilic groups include hydroxyl.

Suitable $R_4$ groups wherein hydroxy is esterfied include: $C_{1-6}$-alkanoyloxy, arylcarbonyloxy, heterocyclylcarbonyloxy, heteroarylcarbonyloxy wherein the $R_1$ group is optionally substituted with between 1 and 3 groups selected from $C_{1-4}$alkyl, $C_{1-4}$alkanoyl, $C_{1-4}$alkanoyl$C_{1-4}$alkyl, $C_{1-4}$alkanoylheterocyclyl, hydroxy, hydroxy$C_{1-4}$alkyl, carboxy, carboxyphenyl, phosphono, phosphono$C_{1-4}$alkyl, amino, amino$C_{1-4}$alkyl, N—$C_{1-4}$alkylamino, N,N-di$C_{1-4}$alkylamino, carbamoyl, carbamoyl$C_{1-4}$alkyl, heterocyclyl, heterocyclyl$C_{1-4}$alkyl, heterocyclylcarbonyl, heterocycl$C_{1-4}$alkanoylamino, carbamoylheterocyclyl, [wherein optional substituents comprising heterocyclyl are optionally further substituted by $C_{1-4}$alkyl, hydroxy$C_{1-4}$alkyl, $C_{1-4}$alkoxy$C_{1-4}$alkyl, $C_{1-4}$alkanoyl and formyl, wherein the carbamoyl and amino optional substituents are optionally further N-substituted by $C_{1-4}$alkyl, di—$C_{1-4}$alkyl, hydroxy$C_{1-4}$alkyl, di-(hydroxy$C_{1-4}$alkyl), carboxy$C_{1-4}$alkyl, and wherein the amino group is optionally substituted by an amino acid residue] with the proviso that when $R_1$ is $C_{1-6}$alkanoyloxy or arylcarbonyloxy $R_1$ is not unsubstituted and $R_1$ is not substituted by $C_{1-4}$alkyl.

More preferred $R_4$ groups wherein hydroxy is esterfied include: carboxypentanoyloxy, 4-carboxyphenylpropanoyloxy; 4-(N-methylpiperazin-1-ylethyl)phenylcarbonyloxy, 4-(piperazin-1-ylethyl) phenylcarbonyloxy, 4-[N-di-(hydroxyethyl)aminomethyl] phenylcarbonyloxy, 3-(N-acetylpiperazin-1-ylethyl) phenylcarbonyloxy, 3-[N-di-(hydroxyethyl)aminomethyl] phenylcarbonyloxy, 4-(N-methylpiperazin-1-ylpropanoylamino)phenylcarbonyloxy, N-methylpiperazin-1-ylcarbonylpropanoyloxy, N-di-(hydroxyethyl) aminocarbonylpropanoyloxy, piperazin-1-ylcarbonylpropanoyloxy, (N-acetylpiperazin-1-yl) carbonylpropanoyloxy, (N-di-(hydroxyethyl) aminocarbonylpropanoyloxy, and 4-(piperazin-1-ylmethyl) phenylcarbonyloxy.

Further preferred $R_1$ groups wherein hydroxy is esterfied include: 4-(N-methylpiperazin-1-ylpropanoylamino) phenylcarbonyloxy, N-methylpiperazin-1-ylcarbonylpropanoyloxy and N-di-(hydroxyethyl) aminocarbonylpropanoyloxy.

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a carbazole derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically acceptable cation, for example a salt with methylamine, dimethylamine, trimethylamine, piperidine, morpholine or tris-(2-hydroxyethyl)amine.

It is to be understood that, insofar as certain of the compounds in the different features of the invention may exist in optically active or racemic forms by virtue of one or more asymmetric carbon atoms, the invention includes in its definition any such optically active or racemic form which possesses the property of inhibiting and/or reversing and/or alleviating the symptoms of angiogenesis and/or any disease states associated with angiogenesis. The synthesis of optically active forms may be carried out by standard techniques of organic chemistry well known in the art, for example by synthesis from optically active starting materials or by resolution of a racemic form. Similarly, activity of these compounds may be evaluated using the standard laboratory techniques referred to hereinafter.

The invention also relates to any and all tautomeric forms of the compounds of the different aspects of the invention that possess the property of inhibiting and/or reversing and/or alleviating the symptoms of angiogenesis and/or any disease states associated with angiogenesis.

It will also be understood that certain compounds of the present invention may exist in solvated, for example hydrated, as well as unsolvated forms. It is to be understood that the present invention encompasses all such solvated forms which possess the property of the property of inhibiting and/or reversing and/or alleviating the symptoms of angiogenesis and/or any disease states associated with angiogenesis.

According to the second aspect of the invention there is provided the use of a compound of Formula (Ib) as a medicament:

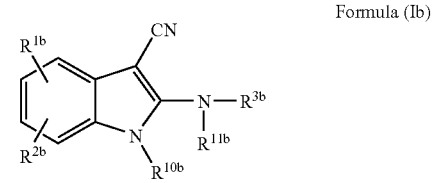

Formula (Ib)

wherein $R^{1b}$ and $R^{2b}$ are independently selected from hydrogen, halogen, —CN, a hydrocarbyl group or a group of Formula (IIb):

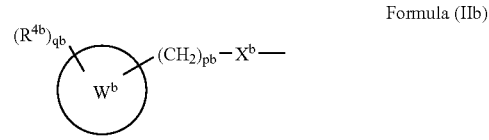

Formula (IIb)

wherein $W^b$ is aryl or a heterocyclic group, $R^{4b}$ is independently selected from hydrogen, halogen, —OH, amino, alkanoylamino, —OPO$_3$H$_2$, or a hydrocarbyl group, wherein the amino group is optionally substituted by an amino acid residue and the hydroxy group is optionally esterified or two $R^{4b}$ groups together form an optionally substituted cyclic or heterocyclic group;

$X^b$ is selected from —S—, —O—, —S(O)—, —S(O$_2$)— and —NH—;

pb is an integer from 0 to 4; and qb is an integer from 1 to 4;

$R^{3b}$ and $R^{10b}$ are independently selected from hydrogen, lower alkyl or a group of Formula (IVb):

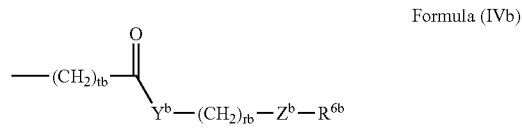

Formula (IVb)

wherein $Y^b$ is selected from —NH—, —O— or a bond;

$Z^b$ is selected from —NH—, —O—, —C(O)— or a bond;

rb is an integer from 0 to 4;

tb is an integer from 0 to 1;

$R^{6b}$ is hydrogen, a hydrocarbyl group or a group of Formula (Vb):

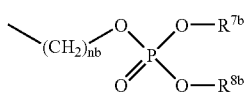

Formula (Vb)

wherein nb is an integer of from 1 to 6, and;
$R^{7b}$ and $R^{8b}$ are independently selected from hydrogen or a hydrocarbyl group; and
$R^{11b}$ is hydrogen or lower alkyl;
or a salt or solvate thereof;
provided that:
i) when $R^{1b}$ is an unsubstituted phenylthio group (Ph—S—), $R^{2b}$ is H, $R^{10b}$ is H and $R^{11b}$ is H then $R^{3b}$ is neither H nor —C(O)—O—CH$_2$CH$_3$.

According to a further feature of the second aspect of the invention there is provided a compound of Formula (Ib) for use in any surgical, therapeutic or diagnostic method practised on a human or animal patient.

According to a further feature of the second aspect of the invention there is provided a compound of Formula (Ib) for use in the preparation of a medicament for use in any surgical, therapeutic or diagnostic method practiced on a human or animal patient.

For each feature of the second aspect of the invention, the surgical, therapeutic or diagnostic method preferably involves the treatment of a human or animal patient to inhibit and/or reverse, and/or to alleviate a symptom of, angiogenesis and/or any disease state associated with angiogenesis. In other words, compounds and derivatives according to the second aspect of the invention are preferably used as vascular damaging and/or anti-angiogenic agents.

Thus, according to the third aspect of the present invention there is provided the use of a compound of Formula (Ic) or a pharmaceutically-acceptable salt or solvate thereof, for the manufacture of a medicament to inhibit and/or reverse and/or alleviate symptoms of angiogenesis and/or any disease state associated with angiogenesis:

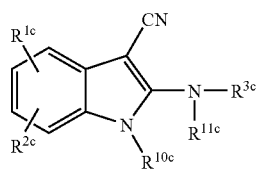

Formula (Ic)

wherein $R^{1c}$ and $R^{2c}$ are independently selected from hydrogen, halogen, —CN, a hydrocarbyl group or a group of Formula (IIc):

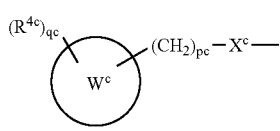

Formula (IIc)

wherein $W^c$ is aryl or a heterocyclic group,
$R^{4c}$ is independently selected from hydrogen, halogen, —OH, amino, alkanoylamino, —OPO$_3$H$_2$, or a hydrocarbyl group, wherein the amino group is optionally substituted by an amino acid residue and the hydroxy group is optionally esterified or two $R^{4c}$ groups together form an optionally substituted cyclic or heterocyclic group;
$X^c$ is selected from —S—, —O—, —S(O)—, —S(O$_2$)— and —NH—;
pc is an integer from 0 to 4; and
qc is an integer from 1 to 4;
$R^{3c}$ and $R^{10c}$ are independently selected from hydrogen, lower alkyl or a group of Formula (IVc):

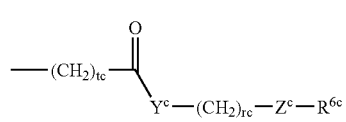

Formula (IVc)

wherein $Y^c$ is selected from —NH—, —O— or a bond;
$Z^c$ is selected from —NH—, —O—, —C(O)— or a bond;
rc is an integer from 0 to 4;
tc is an integer from 0 to 1;
$R^{6c}$ is hydrogen, a hydrocarbyl group or a group of Formula (Vc):

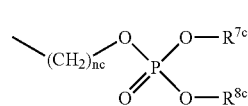

Formula (Vc)

wherein nc is an integer of from 1 to 6, and;
$R^{7c}$ and $R^{8c}$ are independently selected from hydrogen or a hydrocarbyl group; and
$R^{11c}$ is hydrogen or lower alkyl;

According to a further feature of the third aspect of the invention there is provided a method of treatment, in an animal, to inhibit and/or reverse and/or alleviate symptoms of angiogenesis and/or any disease state associated with angiogenesis, comprising administering to said animal a therapeutically effective amount of a compound of Formula (Ic), or a pharmaceutically-acceptable salt or solvate thereof.

An animal is preferably a warm-blooded animal, more preferably a mammal, most preferably a human.

According to a further feature of the third aspect of the invention provides a method of treatment of a patient to inhibit and/or reverse, and/or to alleviate a symptom of, angiogenesis and/or any disease state associated with angiogenesis, the method involving administering to the patient a therapeutically (including prophylactically) effective amount of a compound of Formula (Ia) or derivative thereof, or of a compound of Formula (Ia) (or derivative thereof) in which $R^1$ is an unsubstituted phenylthio group (Ph—S—), $R^2$ is H and $R^3$ is either H or —C(O)—O—CH$_2$CH$_3$.

A patient is preferably a warm-blooded animal, more preferably a mammal, most preferably a human.

The term "therapy" and "therapeutically effective" as used here includes prophylaxis.

A series of preferences for groups of values and for groups of compounds of the invention follow, these relate to compounds of Formula (I) and also relate to the respective groups in compounds of Formula (Ia), Formula (Ib) and Formula (Ic). For example, preferences for $R^1$ also relate to $R^{1a}$, $R^{1b}$, and $R^{1c}$, and preferences for $R^4$ also relate to $R^{4a}$, $R^{5a}$, $R^{4b}$ and $R^{4c}$.

A preferred group of values for $R^1$ in each aspect of the invention is hydrogen, halogen, —CN, lower alkyl or a group of Formula (II):

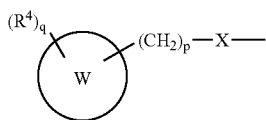

Formula (II)

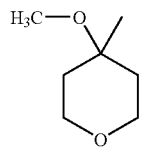

Formula (III)

wherein W, $R^4$, X, p and q are as defined above. More preferably $R^1$ is hydrogen, halogen, lower alkyl or a group of Formula (II) wherein W, $R^4$, X, p and q are as defined above. More preferably $R^1$ is fluoro, chloro, methyl, or a group of Formula (II) wherein W, $R^4$, X, p and q are as defined above. Most preferably $R^1$ is a group of Formula (II) wherein W, $R^4$, X, p and q are as defined above.

A preferred group of values for $R^2$ in each aspect of the invention is hydrogen, halogen, preferably fluoro or chloro, a lower alkyl group, preferably methyl, ethyl, propyl, isopropyl, butyl or t-butyl. More preferably $R^2$ is hydrogen, fluoro, chloro or methyl. Most preferably $R^2$ is hydrogen.

A preferred group of values for W in each aspect of the invention is aryl or a heterocyclic group. More preferably W is phenyl, naphthyl or pyridyl. Most preferably W is phenyl.

A preferred group of values for X in each feature of the invention is —O—, —NH—, —S— or —S(O$_2$)—. More preferably X is —O— or —S—. Most preferably X is —O—.

A preferred group of values for p in each aspect of the invention is when p is 0 or 1. Most preferably p is 0.

A preferred group of values for $R^4$, when q is an integer between 1 and 4, in each aspect of the invention is hydrogen, halogen, —OH, amino, —OPO$_3$H$_2$,or $C_1$–$C_{10}$ alkyl group, a lower alkoxy group, a lower alkanoyl group, a lower alkanoylamino group, a group of Formula (III):

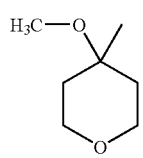

Formula (III)

or a carbonyl group of the Formula —C(O)—$R^9$ where $R^9$ is hydrogen, —OH, a hydrocarbyl group (such as a lower alkyl group or an alkoxy group), wherein the amino group is optionally substituted by an amino acid residue and the hydroxy group is optionally esterified. More preferably $R^4$ is hydrogen, fluoro, —OH, amino, —OPO$_3$H$_2$, a lower alkanoylamino group, or a lower alkoxy group, wherein the amino group is optionally substituted by an amino acid residue and the hydroxy group is optionally esterified. Further preferably $R^4$ is hydrogen, —OH, amino, —OPO$_3$H$_2$, acetylamino, methoxy, serylamino, glutamylamino preferably α-glutanylamino, glycylamino, alanylamino and 4-methylpiperazin-1-ylcarbonylpropanoyloxy. Most preferably $R^4$ is amino, —OH, acetylamino or methoxy.

A preferred group of values for $R^4$, when q is 1, in each aspect of the invention is hydrogen, halogen, —OH, amino, —OPO$_3$H$_2$, or $C_1$–$C_{10}$ alkyl group, a lower alkoxy group, a lower alkanoyl group, a lower alkanoylamino group, a group of Formula (III):

or a carbonyl group of the Formula —C(O)—$R^9$ where $R^9$ is hydrogen, —OH, a hydrocarbyl group such as a lower alkyl group or an alkoxy group), wherein the amino group is optionally substituted by an amino acid residue and the hydroxy group is optionally esterified. More preferably $R^4$ is hydrogen, fluoro, —OH, amino, —OPO$_3$H$_2$, a lower alkanoylamino group, or a lower alkoxy group, wherein the amino group is optionally substituted by an amino acid residue and the hydroxy group is optionally esterified. Further preferably $R^4$ is hydrogen, —OH, amino, —OPO$_3$H$_2$, acetylamino, methoxy, serylamino, glutamylamino preferably α-glutanylamino, glycylamino, alanylamino and 4-methylpiperazin-1-ylcarbonylpropanoyloxy. Most preferably serylamino, α-glutamylamino, glycylamino, —OPO$_3$H$_2$, amino, —OH, acetylamino or methoxy.

A preferred group of values for $R^4$, when q is 2 or 3, in each aspect of the invention is when $R^4$ is independently selected from hydrogen, halogen, —OH, —OPO$_3$H$_2$,or a $C_{1-10}$ alkyl group, or a lower alkoxy group, a lower alkanoyl group, or a carbonyl group of the Formula —C(O)—$R^9$ where $R^9$ is hydrogen, lower alkyl or alkoxy. More preferably $R^4$ is independently selected from hydrogen, fluoro, —OH, —OPO$_3$H$_2$, or a lower alkoxy group. Further preferably $R^4$ is hydrogen, —OH, —OPO$_3$H$_2$ or methoxy. Most preferably $R^4$ is —OPO$_3$H$_2$, —OH or methoxy.

A preferred group of values for q is 2 or 3. More preferably q is 3.

A preferred group of values for $R^3$ in each aspect of the invention is when $R^3$ is hydrogen, lower alkyl or a group of Formula (IV):

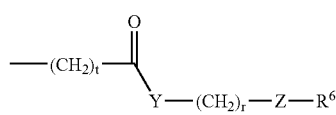

Formula (IV)

wherein t, Y, r, Z and $R^6$ are as defined above. More preferably $R^3$ is hydrogen or a group of Formula (IV). Most preferably $R^3$ is hydrogen.

A preferred group of values for t in each aspect of the invention is 0 or 1. Preferably t is 0.

A preferred group of values for Y in each aspect of the invention is —O— or —NH—. More preferably Y is —O— or a bond. Most preferably —Y— is —O—.

A preferred group of values for r in each aspect of the invention is 2 or 3. Preferably r is 3.

A preferred group of values for Z in each aspect of the invention is —C(O)— or a bond. Preferably Z is a bond.

A preferred group of values for $R^6$ in each aspect of the invention is hydrogen, lower alkyl, a lower alkoxy group, an aryl group, a heterocyclic group or a group of Formula (V), wherein the aryl group and heterocyclic group are optionally substituted by lower alkyl or a lower alkanoyl group:

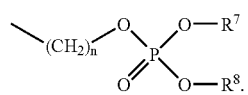

Formula (V)

More preferably $R^6$ is a non-aromatic heterocyclic group, an aryl group or a group of Formula (V), wherein the aryl group and non-aromatic heterocyclic group are optionally substituted by lower alkyl or a lower alkanoyl group. Further preferably $R^6$ is —Ph, morpholino, piperazinyl or a group of Formula (V), wherein the —Ph, morpholino and piperazinyl group are optionally substituted by methyl or acetyl and $R^7$ and $R^8$ are both hydrogen. Most preferably $R^6$ is —Ph, morpholino or 4-methyl-piperazin-1-yl.

A preferred group of values for n in each aspect of the invention is 2 or 3. Preferably n is 2.

A preferred group of values for $R^7$ and $R^8$ in each aspect of the invention is $R^7$ and $R^8$ are independently selected from hydrogen or an alkaryl group, preferably —$(CH_2)_m$— Ph where m is an integer of from 1 to 6, preferably m is 1. More preferably $R^7$ and $R^8$ are independently selected from hydrogen or benzyl (—$CH_2$—Ph). Preferably $R^7$ and $R^8$ are both hydrogen.

A preferred group of values for $R^{10}$ in each aspect of the invention is hydrogen, lower alkyl or a group of Formula (IV), wherein t, Y, r, Z and $R^6$ are as defined above. More preferably $R^{10}$ is hydrogen, lower alkyl or lower carbamoylalkyl group. Most preferably $R^{10}$ is hydrogen, methyl or carbamoylmethyl.

A preferred group of values for a group of Formula (IV) is phenoxycarbonyl, phosphonooxyethylaminocarbonyl, 4-methylpiperazin-1-ylpropoxycarbonyl, carbarnoylmethyl, 4-acetyl-piperazin-1-ylethoxycarbonyl, 4-methyl-piperazin-1-ylcarbonylpropanoyl and morpholinoethoxycarbonyl. Preferably phenoxycarbonyl, 4-methylpiperazin-1-ylpropoxycarbonyl or carbamoylmethyl.

Preferably only one of $R^3$ and $R^{10}$ is a group of Formula (IV).

A preferred group of values for $R^{11}$ in each aspect of the invention is hydrogen or lower alkyl. More preferably $R^{11}$ is hydrogen or methyl. Most preferably $R^{11}$ is hydrogen.

In the following preferred groups of compounds of each aspect of the invention values for $R^1$, $R^2$, $R^3$, $R^4$, $R^5$, $R^6$, $R^7$, $R^8$, $R^9$, $R^{10}$, $R^{11}$, n, m, p, q, r, t, W, X, Y and Z are as hereinbefore defined, unless specifically defined with a preferred group of compounds.

A further preferred group of compounds of each aspect of the invention described herein, comprise compounds wherein:

$R^1$ is a group of Formula (II);
X is —O—;
p is 0 or 1; and
W is phenyl;
or a salt or solvate thereof.

A further preferred group of compounds of each aspect of the invention described herein, comprise compounds wherein:

$R^1$ is a group of Formula (II);
X is —NH—;
p is 0 or 1; and
W is phenyl;
or a salt or solvate thereof.

A further preferred group of compounds of each aspect of the invention described herein, comprise compounds wherein:

$R^1$ is a group of Formula (II);
X is —S—, —SO— or —S($O_2$)—, preferably X is —S— or —S($O_2$)—, most preferably X is —S—;
p is 0 or 1; and
W is phenyl;
or a salt or solvate thereof.

A further preferred group of compounds of each aspect of the invention described herein, comprise compounds wherein:

$R^1$ is a group of Formula (II);
X is —S—, —S($O_2$)—, —O— or —NH—; preferably X is —O— or —S—; most preferably X is —O—;
p is 0 or 1; and
W is phenyl;
$R^4$ is hydrogen, —OH, amino, —$OPO_3H_2$, or a $C_{1-4}$alkoxy group, wherein the amino group is optionally substituted by an amino acid residue and the hydroxy group is optionally esterified;
q is an integer between 1 and 3;
or a salt or solvate thereof.

A further preferred group of compounds of each aspect of the invention described herein, comprise compounds wherein:

$R^1$ is a group of Formula (II);
X is —S—, —S($O_2$)—, —O— or —NH—; preferably X is —O— or —S—; most preferably X is —O—;
p is 0 or 1;
W is phenyl;
$R^4$ is an amino group or —$OPO_3H_2$, wherein the amino group is substituted by an amino acid residue. Preferably $R^4$ is serylamino, glutamylamino, glycylamino, or alanylamino. Most preferably $R^4$ is serylamino, α-glutamylamino, glycylamino, or alanylamino; and
q is 1;
or a salt or solvate thereof.

A further preferred group of compounds of each aspect of the invention described herein, comprise compounds wherein:

$R^1$ is a group of Formula (II);
X is —S—, —S($O_2$)—, —O— or —NH—; preferably X is —O— or —S—; most preferably X is —O—;
p is 0 or 1; and
W is phenyl;
$R^4$ is independently selected from hydrogen, —OH, —$OPO_3H_2$, or a $C_{1-4}$alkoxy group, preferably $R^4$ is independently selected from —$OPO_3H_2$, methoxy or ethoxy, most preferably $R^4$ is methoxy;
q is an integer between 1 and 4, preferably q is 2 or 3, most preferably q is 3;
or a salt or solvate thereof.

A further preferred group of compounds of each aspect of the invention described wherein, comprise compounds wherein:

$R^3$ and $R^{10}$ are independently selected from hydrogen, methyl, ethyl or a group of Formula (IV), preferably methyl or a group of Formula (IV);
or a salt or solvate thereof.

A further preferred groups of compounds of each aspect of the invention described herein comprise compounds wherein:

$R^3$ is a group of Formula (IV) and $R^{10}$ is hydrogen or lower alkyl or $R^3$ is hydrogen or lower alkyl and $R^{10}$ is a group of Formula (IV);

t is 0 or 1, preferably 0;

Y is —NH— or —O—, preferably Y is —O—;

r is an integer between 2 and 4, preferably 2 or 3;

Z is a bond; and $R^6$ is a —Ph or a non-aromatic heterocyclic group, wherein —Ph and the non-aromatic heterocyclic group are optionally substituted by lower alkyl or a lower alkanoyl group, preferably $R^6$ is a non-aromatic heterocyclic group optionally substituted by lower alkyl or a lower alkanoyl group;

or a salt or solvate thereof.

Preferred compounds of the invention include:

2-phenoxycarbonylamino-5-phenylsulphanyl-1H-indole-3-carbonitrile;

5-(4-hydroxyphenylsulphanyl)-2-amino-1H-indole-3-carbonitrile;

5-(3,6-dimethoxyphenylsulphanyl)-2-amino-1H-indole-3-carbonitrile;

5-phenylsulphanyl-2-(4-methylpiperazin-1-ylpropoxycarbonylamino)-1H-indole-3-carbonitrile;

5-phenylsulphanyl-1-(4-methylpiperazin-1-ylpropoxycarbonyl)-2-amino-1H-indole-3-carbonitrile;

6-benzyloxy-2-amino-1H-indole-3-carbonitrile;

5-[4-(4-methylpiperazin-1-yl-4-oxobutanoyloxy)phenoxy]-2-amino-1H-indole-3-carbonitrile;

5-(4-glycylaminophenoxy)-2-amino-1H-indole-3-carbonitrile;

5-(4-alanylaminophenoxy)-2-amino-1H-indole-3-carbonitrile;

5-(4-glutamylaminophenoxy)-2-amino-1H-indole-3-carbonitrile;

5-(3-glycylbenzyloxy)-2-amino-1H-indole-3-carbonitrile;

5-(4-hydroxyphenoxy)-2-amino-1H-indole-3-carbonitrile;

5-(4-phosponooxyphenoxy)-2-amino-1H-indole-3-carbonitrile;

5-(3-serylbenzyloxy)-2-amino-1H-indole-3-carbonitrile;

5-(4-acetylaminophenoxy)-2-amino-1H-indole-3-carbonitrile; and 5-(4-serylaminophenoxy)-2-amino-1H-indole-3-carbonitrile;

or salt or solvate thereof.

More preferred compounds of the invention include:

5-(4aminophenoxy)-2-amino-1H-indole-3-carbonitrile; and 5-(3,4,5-trimethoxyphenoxy)-2-amino-1H-indole-3-carbonitrile, or salt or solvate thereof.

Most preferred compounds of the invention include:

5-(3,4-dimethoxyphenylsulphanyl)-2-amino-1H-indole-3-carbonitrile; and (Example 3)

5-(3,4,5-trimethoxyphenoxy)-2-amino-1H-indole-3-carbonitrile; (Example 11)

or salt or solvate thereof.

In any aspect of the invention it is desirable to include in the compound of the invention, at any appropriate position, a water solubilising group such as (but not limited to) a phosphate, sulphate or sugar group, to enhance the bioavailability of the compound on administration to a patient.

The first aspect of the invention also encompasses derivatives of compounds of Formula (I), such as pharmaceutically acceptable salts and/or ionic forms (for instance where a terminal hydroxyl group is actually present as —O⁻ or a terminal amine is in it's protonated form), co-ordination complexes for example with metal ions, hydrated forms, labelled forms for instance for use in diagnostic methods and pharmaceutical precursors which are convertible, either in vitro or in vivo, into the relevant compound.

A compound of the invention or a pharmaceutically-acceptable salt, or solvate thereof, may be prepared by any process known to be applicable to the preparation of chemically related compounds. Such processes, when used to prepare a compound of the invention or a pharmaceutically-acceptable salt, or solvate thereof, are provided as a further feature of the invention and are illustrated by the following representative examples in which $R^1$, $R^2$, $R^3$, $R^4$, $R^5$, $R^6$, $R^7$, $R^8$, $R^9$, $R^{10}$, $R^{11}$, m, n, p, q, r, t, W, X, Y and Z have the same meaning as herein before defined. The reader is referred to Advanced Organic Chemistry, 4$^{th}$ Edition, by Jerry March, published by John Wiley & Sons 1992, for general guidance on reaction conditions and reagents. The reader is referred to Protective Groups in Organic Synthesis 2$^{nd}$ Edition, by Green et at, published by John Wiley & Sons for general guidance on protecting groups.

Thus, according to the fourth aspect of the invention there is provided a process for preparing a compound of Formula (I), or salt, or solvate thereof, which process (wherein $R^1$, $R^2$, $R^3$, $R^4$, $R^5$, $R^6$, $R^7$, $R^8$, $R^9$, $R^{10}$, $R^{11}$, m, n, p, q, r, t, W, X, Y and Z are unless otherwise specified as defined in Formula (I)) comprises:

a) for compounds of Formula (I) wherein $R^1$ is of the Formula (II) and X is —O—, —S— or —NH—, reacting a compound of Formula (A) with a compound of Formula (B):

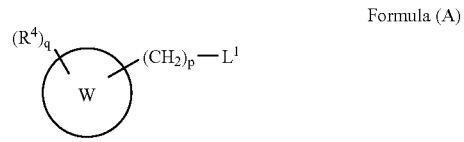

Formula (A)

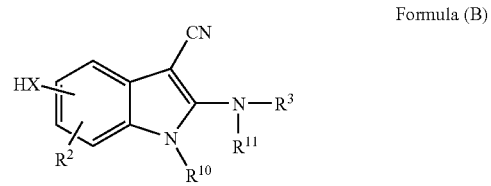

Formula (B)

wherein $L^1$ is a leaving group;

b) for compounds of Formula (I) in which $R^3$ is hydrogen and $R^{11}$ is hydrogen may be prepared by reduction followed by ring closure of compounds of Formula (C):

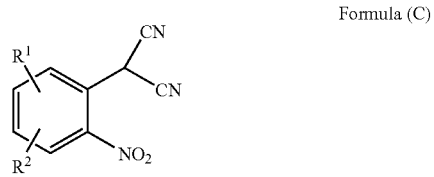

Formula (C)

c) for compounds of Formula (I) wherein $R^{10}$ is lower alkyl, reacting a compound of Formula (I) wherein $R^{10}$ is hydrogen with a suitable alkylhalide, d) for compounds of Formula (I) wherein $R^1$ is of the Formula (II) and X is —S(O)—, —S(O$_2$)—, oxidising a compound of Formula (D):

Formula (D)

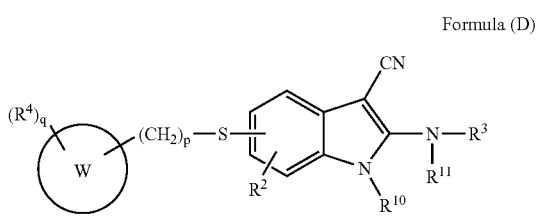

e) for compounds of Formula (I) in which $R^3$ is a group of Formula (IV) may be prepared by the reaction of compounds of Formula (I) in which $R^3$ is hydrogen with compounds of Formula (F) below, in which $L^2$ is a leaving group:

Formula (F)

$$L^2-(CH_2)_t-\overset{O}{\underset{}{C}}-Y-(CH_2)_r-Z-R^6$$

and thereafter if necessary:
  i) converting a compound of Formula (I) into another compound of Formula (I);
  ii) removing any protecting groups;
  iii) forming a salt, or solvate.

According to a further feature of the fourth aspect of the invention there is provided the processes a), b), c), d) and e) described above for the preparation of compounds of the Formula (I), or a salt, or solvate thereof.

Specific reaction conditions for the above reactions are as follows:

Process a) Compounds of Formula (A) and compound of Formula (B) can be reacted together in an organic solvent, at a temperature between room temperature and about 80° C., optionally in the presence of a base such as sodium hydride, potassium carbonate or triethylamine.

Process b) The conditions for reduction of a compound of Formula (C) are well known in the art. Examples of reducing agents include hydrogen and a hydrogenation catalyst (for example palladium on carbon), iron and acetic acid, and zinc and hydrochloric acid. The reaction is preferably carried out in the presence of a suitable solvent such as an alcohol, for example methanol or ethanol, and at a temperature in the range of 0–80° C., preferably at or near room temperature. Further examples of reducing conditions include sodium dithionite in the presence of a base, preferably sodium bicarbonate in a suitable solvent such as DMF or N-methyl-pyrrolidone.

Compounds of Formula (C) can be prepared by displacement of a halogen atom, preferably F or Cl, from compounds of Formula (E), using a salt of malononitrile, preferably the sodium salt:

Formula (E)

$$\underset{R^2}{\overset{R^1}{\text{(benzene ring with halogen and NO}_2\text{)}}}$$

A method for reduction and ring closure of a compound of Formula (C) can be found in U.S. Pat. No. 4,533,672.

Process c) Compounds of Formula (I) wherein $R_2$ is hydrogen and a suitable alkyl halide may be reacted together in a suitable organic solvent such as DMF or DMSO, in the presence of a base, such as sodium hydride or potassium carbonate at a temperature between about room temperature and about 80° C.

Process d) The oxidization of a compound of Formula (D) can be carried out, for example, by reaction with metachloroperbenzoic acid (MCPBA) is the presence of a suitable solvent such as dichloromethane at ambient temperature. If an excess of MCPBA is used a compound of Formula (I) wherein X is —S($O_2$)— is obtained.

Process e) Compounds of Formula (I) in which $R^3$ is hydrogen can be reacted with compounds of Formula (F) under conditions well known in the art. For example $L^2$ may be —Cl or p-nitrophenoxy. When $L^2$ is Cl this is carried out in the presence of a base, preferably pyridine The synthesis of a compound of Formula (I) in which $R^1$, $R^2$ and $R^3$ are all hydrogen (2-aminoindole-3-carbonitrile) is described by Eger et al in *Liebigs Ann. Chem.* 1993, 465–470.

The compounds used as starting points for the reactions described above are commercially available or they are known compounds or they are prepared by processes known in the art.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed, for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

According to the fifth aspect of the invention there is provided a pharmaceutical composition comprising a compound of Formula (I) or pharmaceutically acceptable salt or solvate thereof or a compound of Formula (I*a*) or pharmaceutically-acceptable derivative thereof.

According to a further feature of the fifth aspect of the invention there is provided a pharmaceutical composition comprising a compound of Formula (I) or pharmaceutically acceptable salt or solvate thereof or a compound of Formula (I*a*) or pharmaceutically-acceptable derivative thereof, in admixture with a pharmaceutically-acceptable diluent or carrier.

In order to use a compound of Formula (I) or pharmaceutically acceptable salt or solvate thereof or a compound of Formula (I*a*) or pharmaceutically-acceptable derivative thereof, for the therapeutic treatment (including prophylactic treatment) of mammals including humans, it is normally formulated in accordance with standard pharmaceutical practice as a pharmaceutical composition.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate), anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 µm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula (I) will naturally vary according to the nature and severity of the conditions, the age and sex of the animal or patient and the route of administration, according to well known principles of medicine.

In using a compound of the Formula (I) for therapeutic or prophylactic purposes it will generally be administered so that a daily dose in the range, for example, 0.5 mg to 50 mg per kg body weight is received, given if required in divided doses. In general lower doses will be administered when a parenteral route is employed. Thus, for example, for intravenous administration, a dose in the range, for example, 0.2 mg to 10 mg per kg body weight will generally be used. Typically, intravenous doses of about 10 mg to 500 mg per patient of a compound of this invention will be used.

The compounds of this invention may be used in combination with other drugs and therapies used to inhibit and/or reverse and/or alleviate symptom of angiogenesis and/or any disease state associated with angiogenesis. Examples of such disease states include: cancer, diabetes, psoriasis, rheumatoid arthritis, Kaposi's sarcoma, haemangioma, acute and chronic nephropathies, atheroma, arterial restenosis, autoimmune diseases, acute inflammation, endometriosis, dysfunctional uterine bleeding and ocular diseases with retinal vessel proliferation.

If formulated as a fixed dose such combination products employ the compounds of this invention within the dosage range described herein and the other pharmaceutically-active agent within its approved dosage range. Sequential use is contemplated when a combination formulation is inappropriate.

Possible uses for the pharmaceutical composition include both therapeutic and diagnostic uses. In particular, it may be used to treat and/or diagnose any condition which is related to (ie, which is or can be caused or mediated, directly or indirectly, by, or which is in any way associated with) angiogenesis or vasculature formation, especially of tumours.

A therapeutic treatment method in which a compound or derivative according to the invention may be used involves the administration to a patient suffering from a relevant condition of a therapeutically (which includes prophylactically) effective amount of the compound or derivative, preferably in the form of a pharmaceutical composition according to the fifth aspect of the invention. "Effective amount" means an amount sufficient to cause a benefit (which may be prophylactic) to the patient or at least to cause a change in the patient's condition, eg, to cause a medically significant inhibition of tumour development. The actual amount administered to the patient, and the rate and time-course of administration, will depend on the nature of the patient, the nature and severity of the condition, the administration method used, etc. Appropriate values can be selected by the trained medical practitioner. The compound or derivative may be administered alone or in combination with other treatments, either simultaneously or sequentially. It may be administered by any suitable route, preferably orally. It may be administered directly to a suitable site or in a manner in which it targets a particular site—suitable targeting methods are already known.

A diagnostic method according to the invention might involve the use of the compound or derivative to determine, either qualitatively or quantitatively, the existence of a particular medical condition or change in condition. Such a method may be carried out either in vitro or in vivo. One or more of the materials used in the method may be appropriately labelled.

According to a sixth aspect of the present invention there is provided a method for producing a pharmaceutical composition according to the fifth aspect of the invention, said method comprising providing (for example by synthesising) a compound of Formula (I) or pharmaceutically-acceptable salt or solvate thereof or a compound of Formula (Ia) or pharmaceutically-acceptable derivative thereof, and then mixing it with one or more pharmaceutically acceptable adjuvants, and/or with one or more other therapeutically or diagnostically active agents.

According to a seventh aspect of the present invention there is provided a compound of Formula (I) or pharmaceutically-acceptable salt or solvate thereof or a compound of Formula (Ia) or pharmaceutically-acceptable derivative thereof, preferably in the form of a pharmaceutical composition according to the fifth aspect of the invention, when dosed in divided doses (also known as split doses) produces a greater anti-tumour effect than when a single dose is given.

Anti-tumour effects of a method of treatment of the present invention include but are not limited to, inhibition of tumour growth, tumour growth delay, regression of tumour, shrinkage of tumour, increased time to regrowth of tumour on cessation of treatment, slowing of disease progression. It is expected that when a method of treatment of the present invention is administered to a warm-blooded animal such as a human, in need of treatment for cancer involving a solid tumour, said method of treatment will produce an effect, as measured by, for example, one or more of: the extent of the anti-tumour effect, the response rate, the time to disease progression and the survival rate.

According to a further feature of the seventh aspect of the present invention there is provided a method for the production of a vascular damaging effect in a warm-blooded animal such as a human, which comprises administering to said animal in divided doses an effective amount of a compound of Formula (I) or pharmaceutically-acceptable salt or solvate thereof or a compound of Formula (Ia) or pharmaceutically-acceptable derivative thereof, preferably in the form of a pharmaceutical composition according to the fifth aspect of the present invention.

According to a further feature of the seventh aspect of the present invention there is provided a method for the treatment of a cancer involving a solid tumour in a warm-blooded animal such as a human, which comprises administering to said animal in divided doses an effective amount of a compound of Formula (I) or pharmaceutically-acceptable salt or solvate thereof or a compound of Formula (Ia) or pharmaceutically-acceptable derivative thereof, preferably in the form of a pharmaceutical composition according to the fifth aspect of the present invention.

According to a further feature of the seventh aspect of the present invention there is provided a medicament comprising two or more fractions of doses of a compound of Formula (I) or pharmaceutically-acceptable salt or solvate thereof or a compound of Formula (Ia) or pharmaceutically-acceptable derivative thereof, preferably in the form of a pharmaceutical composition according to the fifth aspect of the present invention, which together add up to a total daily dose, for administration in divided doses for use in a method of treatment of a human or animal body by therapy.

According to a further feature of the seventh aspect of the present invention there is provided a kit comprising two or more fractions of doses of a compound of Formula (I) or pharmaceutically-acceptable salt or solvate thereof or a compound of Formula (Ia) or pharmaceutically-acceptable derivative thereof, preferably in the form of a pharmaceutical composition according to the fifth aspect of the present invention, which together add up to a total daily dose, for administration in divided doses.

According to a further feature of the seventh aspect of the present invention there is provided a kit comprising:
  a) two or more fractions of doses of a compound of Formula (I) or pharmaceutically-acceptable salt or solvate thereof or a compound of Formula (Ia) or pharmaceutically-acceptable derivative thereof, which together add up to a total daily dose, in unit dosage forms for administration in divided doses; and
  b) container means for containing said dosage forms.

According to a further feature of the seventh aspect of the present invention there is provided a kit comprising:
  a) two or more fractions of doses of a compound of Formula (I) or pharmaceutically-acceptable salt or solvate thereof or a compound of Formula (Ia) or pharmaceutically-acceptable derivative thereof, which together add up to a total daily dose, together with a pharmaceutically acceptable excipient or carrier, in unit dosage forms; and
  b) container means for containing said dosage forms.

According to a further feature of the seventh aspect of the present invention there is provided the use of compound of Formula (I) or pharmaceutically-acceptable salt or solvate thereof or a compound of Formula (Ia) or pharmaceutically-acceptable derivative thereof in the manufacture of a medicament for administration in divided doses for use in the production of a vascular damaging effect in a warm-blooded animal such as a human.

According to a further feature of the seventh aspect of the present invention there is provided the use of a compound of Formula (I) or pharmaceutically-acceptable salt or solvate thereof or a compound of Formula (Ia) or pharmaceutically-acceptable derivative thereof in the manufacture of a medicament for administraton in divided doses for use in the production of an anti-cancer effect in a warm-blooded animal such as a human.

According to a further feature of the seventh aspect of the present invention there is provided the use of a compound of Formula (I) or pharmaceutically-acceptable salt or solvate thereof or a compound of Formula (Ia) or pharmaceutically-acceptable derivative thereof in the manufacture of a medicament for administration in divided doses for use in the production of an anti-tumour effect in a warm-blooded animal such as a human.

Divided doses, also called split doses, means that the total dose to be administered to a warm-blooded animal, such as a human, in any one day period (for example one 24 hour period from midnight to midnight) is divided up into two or more fractions of the total dose and these fractions are administered with a time period between each fraction of about greater than 0 hours to about 10 hours, preferably about 1 hour to about 6 hours, more preferably about 2 hours to about 4 hours. The fractions of total dose may be about equal or unequal.

Preferably the total dose is divided into two parts which may be about equal or unequal.

The time intervals between doses may be for example selected from:
  about 1 hour, about 1.5 hours, about 2 hours, about 2.5 hours, about 3 hours, about 3.5 hours, about 4 hours, about 4.5 hours, about 5 hours, about 5.5 hours and about 6 hours.

The time intervals between doses may be any number (including non-integers) of minutes between greater than 0 minutes and 600 minutes, preferably between 45 and 375 minutes inclusive. If more than two doses are administered the time intervals between each dose may be about equal or unequal.

Preferably two doses are given with a time interval in between them of greater than or equal to 1 hour and less than 6 hours.

More preferably two doses are given with a time interval in between them of greater than or equal to two hours and less than 5 hours.

Yet more preferably two doses are given with a time interval in between them of greater than or equal to two hours and less than or equal to 4 hours.

Particularly the total dose is divided into two parts which may be about equal or unequal with a time interval between doses of greater than or equal to about two hours and less than or equal to about 4 hours.

More particularly the total dose is divided into two parts which may be about equal with a time interval between doses of greater than or equal to about two hours and less than or equal to about 4 hours.

For the avoidance of doubt the term 'about' in the description of time periods means the time given plus or minus 15 minutes, thus for example about 1 hour means 45 to 75 minutes, about 1.5 hours means 75 to 105 minutes. Elsewhere the term 'about' has its usual dictionary meaning.

An anti-vascular/anti-angiogenic treatment in accordance with the present invention may be applied as a sole therapy or may involve, in addition to the compound of Formula (I) or pharmaceutically-acceptable salt or solvate thereof or a compound of Formula (Ia) or pharmaceutically-acceptable derivative thereof, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the anti-vascular/anti-angiogenic treatment according to the invention may be, for example, surgery, radiotherapy or chemotherapy. Such chemotherapy may include the following categories of therapeutic agent:

i) anti-angiogenic agents that work by different mechanisms from the compounds of Formula (I) (for example linomide, inhibitors of integrin $\alpha v\beta 3$ function, angiostatin, endostatin, razoxin, thalidomide) and including vascular endothelial growth factor (VEGF) receptor tyrosine kinase inhibitors (RTKIs) (for example those described in international patent applications publication nos. WO-97/22596, WO-97/30035, WO-97/32856 and WO-98/13354, the entire disclosure of which documents is incorporated herein by reference);

ii) cytostatic agents such as anti-oestrogens (for example tamoxifen, toremifene, raloxifene, droloxifene, iodoxyfene), progestogens (for example megestrol acetate), aromatase inhibitors (for example anastrozole, letrazole, vorazole, exemestane), anti-progestogens, anti-androgens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example epidermal growth factor (EGF), platelet derived growth factor and hepatocyte growth factor such inhibitors include growth factor antibodies, growth factor receptor antibodies, tyrosine kinase inhibitors and serine/threonine kinase inhibitors);

iii) biological response modifiers (for example interferon);

iv) antibodies (for example edrecolomab); and v) anti-proliferative/anti-neoplastic drugs and combinations thereof, as used in medical oncology, such as anti-metabolites (for example anti-folates like methotrexate, fluoropyrimidines like 5-fluorouracil, purine and adenosine analogues, cytosine arabinoside); anti-tumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); anti-mitotic agents (for example vinca alkaloids like vincristine and taxoids like taxol, taxotere); enzymes (for example asparaginase); thymidylate synthase inhibitors (for example raltitrexed); topoisomerase inhibitors (for example epipodophyllotoxins like etoposide and teniposide, amsacrine, topotecan, irinotecan).

As stated above compounds of Formula (I) or Formula (Ia) are of interest for their potential vascular damaging effects. They are expected to be useful in the prophylaxis and treatment of a wide range of disease states where inappropriate angiogenesis occurs including cancer, diabetes, psoriasis, rheumatoid arthritis, Kaposi's sarcoma, haemangioma, acute and chronic nephropathies, atheroma, arterial restenosis, autoimmune diseases, acute inflammation, endometriosis, dysfunctional uterine bleeding and ocular diseases with retinal vessel proliferation. In particular the compounds are expected to slow advantageously the growth of primary and recurrent solid tumours of, for example, the colon, breast, prostate, lungs and skin.

In addition to their use in therapeutic medicine, compounds of Formula (I) and their pharmaceutically acceptable derivatives may also be useful as pharmacological tools in the development and standardisation of in vitro and in vivo test systems for the evaluation of the effects of vascular damaging agents in laboratory animals such as cats, dogs, rabbits, monkeys, rats and mice, as part of the search for new therapeutic agents.

Compounds of Formula (I) and compounds of Formula (Ia) encompass vascular damaging agents and pro-drugs of vascular damaging agents. Pro-drugs of vascular damaging agents are believed to be cleaved in-vivo. Without being bound by theoretical considerations these pro-drugs may have lower activity in the in-vitro colchicine binding site competitive assay, than would be anticipated when the activity of these compounds is measured in cell based assays or in-vivo.

Biological Assays (i) Colchicine Binding Site Competitive Assay Kit.

The ability of a ligand to bind specifically to the coichicine binding site on tubulin, an indicator of the vascular damaging activity, was assessed using a size exclusion chromatography assay kit from "Cytoskeleton" (1650 Fillmore St. #240, Denver, Colo. 80206, U.S.A.) Catalogue number of kit: BK023.

The following reagents were used:

tubulin buffer, to give 0.1 mM GTP, 0.5 mM $MgCl_2$, 0.5 mM EGTA, 40 mM PIPES buffer at pH6.9 in the final reaction mix;

purified tubulin protein from bovine brain at 1 mg/ml in tubulin buffer;

0.02 mM fluorescent coichicine in tubulin buffer [FITC (fluorescein isothiocyanate)-labelled];

2 mM colchicine in tubulin buffer;

0.2 mM vinblastine in tubulin buffer; and

G-25 Sephadex™ Fine-particle size 34–138 μm.

The reaction was performed as follows:
8 µl of test compound (dissolved in DMSO) was gently mixed with 150 µl of tubulin. This was then incubated at 37° C. for 30 minutes. Then 4 µl of the fluorescent colchicine was added, the incubation mix vortexed for 5 seconds and then incubated for a further 30 minutes at 37° C. At the end of the reaction incubation size exclusion chromatography was performed to separate the tubulin with fluorescent colchicine bound from the free, unbound colchicine. If a test compound inhibited fluorescent colchicine binding then a reduced signal is measured and the compound is confirmed as a colchicine site binding moiety.

Chromatography was performed as follows, using chromatography columns filled with 3 mls of G-25 Sephadex™ Fine slurry. The incubation mixture was pipetted onto the column and up to 12 elutions of 160 µl were collected. The fluorescence of the tubulin-containing fractions was detected on a spectrophotometer which excites at 485 nm and emits at 535 nm. Control incubations were also performed, 8 µl DMSO (negative control) and 8 µl colchicine stock (positive competition control), instead of the 8 µl of test compound in the incubation mixture.

The degree of competition of colchicine binding by either unlabelled colchicine or test compound was calculated relative to the DMSO negative control.

(ii) HUVEC Detachment Assay

Compounds according to the invention are expected to be able to damage vasculature, such as tumour vasculature, that has been newly formed whilst leaving normal, mature vasculature unaffected. The identification of compounds which can selectively, and preferably potently, damage newly-formed vasculature is desirable and is the subject of the present invention. The ability of the compounds to act in this way may be assessed, for example, using the procedure set out below:

This assay examined the effects of compounds on the adherence of HUVECs (Human umbilical cord vein endothelial cells) to tissue culture plasticware.

HUVECs (supplied by TCS Biologicals Ltd, Buckingham, United Kingdom) were plated in 0.2% gelatin-coated 12 well tissue culture plates at a concentration of $3 \times 10^4$ cells per well in 1 ml TCS medium. After 24 hours, when the cells were at ~30% confluency, they were dosed with a compound under test for 40 minutes at 37° C., 5% $CO_2$. After this incubation the medium containing drug was pipetted off, and the cells were then gently washed in 2 mls of HBSS (Hanks' Balanced Salt Solution purchased from Life Technologies Ltd, Paisley UK; Catalogue # 24020-083) to remove any detached cells. The washing solution was then removed, and the adherent cells remaining were trypsinised using 300 µl of 1×Trypsin-EDTA solution (Life Technologies Ltd, Paisley, UK; Catalogue # 43500-019) at ambient temperature for 2 minutes. The trypsinised cells were then made up to 1 ml with TCS Biologicals medium, then centrifuged at 2000 rpm for 2 minutes. The cell pellet was then resuspended in a volume of 50 µl of TCS Biologicals medium. Total cell counts were obtained by counting the cells on a haemocytometer. The amount of cell detachment was calculated by comparing the number of cells remaining attached following treatment with the number in undosed control wells.

Although the pharmacological properties of the compounds of the Formula (I) vary with structural change as expected, in general compounds of the Formula (I) possess an activity in the colchicine binding site competitive assay of greater than 20% competition at a dose of compound of 10 µM and an activity in the HUVEC detachment assay of between 15–70% detachment at a dose of compound of 100 µM. For example 5-(4-hydroxyphenylsulphanyl)-2-amino-1H-indole-3-carbonitrile (Example 2) has an activity of 36% in the colchicine binding site competitive assay at 10 µM and 55% in the cell detachment assay at 100 µM and 6-methyl-5-fluoro-2-amino-1H-indole-3-carbonitrile (Example 8) has an activity of 31% in the colchicine binding site competitive assay at 10 µM and 34% in the cell detachment assay at 100 µM.

The invention will now be illustrated by the following non-limiting Examples in which, unless otherwise stated:-

(i) evaporations were carried out by rotary evaporation in vacuo and work-up procedures were carried out after removal of residual solids such as drying agents by filtration;

(ii) operations were carried out at ambient temperature, that is in the range 18–25° C. and under an atmosphere of an inert gas such as argon or nitrogen;

(iii) yields are given for illustration only and are not necessarily the maximum attainable;

(iv) the structures of the end-products of the Formula (I) were confirmed by nuclear (generally proton) magnetic resonance (NMR) and mass spectral (MS or LCMS) techniques; proton magnetic resonance chemical shift values were measured on the delta scale and peak multiplicities are shown as follows: s, singlet; d, doublet; t, triplet; m, multiplet; br, broad; q, quartet; quin, quintet;

(v) intermediates were not generally fully characterised and purity was assessed by thin layer chromatography (TLC), high-performance liquid chromatography (HPLC), infra-red (IR) or NMR analysis;

(vi) flash chromatography was performed on silica (Merck Keiselgel: Art.9385);

(vii) concentrations of solvent in the elemental analyses are quoted in molar (M);

(viii) HP20SS resin (DIAION® HP20SS) was obtained from Mitsubishi Chemical America Inc.

| Abbreviations | |
|---|---|
| Dimethylacetamide | DMA |
| 4-Dimethylaminopyridine | DMAP |
| Dimethylformamide | DMF |
| Dimethyl sulphoxide | DMSO |
| 1-(3-Dimethylaminopropyl)-3-ethylcarbodiimide hydrochloride | EDCI |
| Liquid chromatographic mass spectroscopy | LCMS |
| Mass spectroscopy | MS |
| N-(9-fluorenylmethoxycarbonyl) | N-FMOC |
| N-methyl-pyrrolidone | NMP |
| Tetrahydrofuran | THF |

EXAMPLE 1
2-Phenoxycarbonylamino-5-phenylsulphanyl-1H-indole-3-carbonitrile

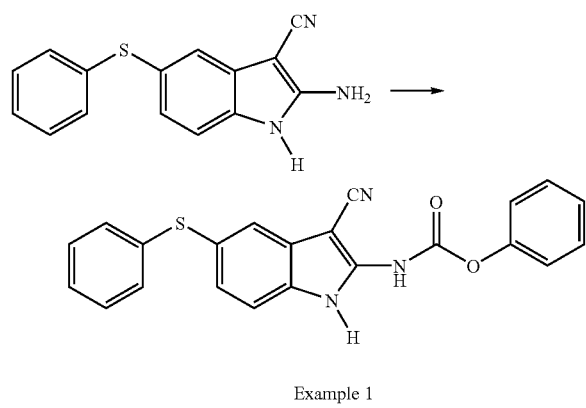

Example 1

A solution of 5-phenylsulphanyl-2-amino-1H-indole-3-carbonitrile (0.43 g; 1.62 mmol) [Amphethinile, U.S. Pat. No. 4,533,672] in THF (5 ml) and pyridine (0.17 ml; 2.1 mmol) under argon was cooled to 0° C. and treated dropwise with phenyl chloroformate (0.25 ml; 2.0 mmol). The mixture was allowed to warm to room temperature overnight. After dilution with $CH_2Cl_2$ the organic phase was washed with water, then brine and dried over $MgSO_4$. The residue was purified by flash chromatography eluting with increasingly polar mixtures of $Et_2O/CH_2Cl_2$ (5 to 10% $Et_2O$) to give 2-phenoxycarbonylamino-5-phenylsulphanyl-1H-indole-3-carbonitrile as a beige solid (310 mg).

Yield: 50%

$^1$H NMR spectrum ($CDCl_3$): 7.14–7.35 (m, 10H); 7.44 (t, 2H); 7.71 (d, 1H); 10.83 (s, 1H); 10.99 (br s, 1H).

MS-ESI: 408 [MNa]$^+$

| Elemental analysis: | Found | C 67.14 | H 3.94 | N 10.76 | S 7.79 |
|---|---|---|---|---|---|
| $C_{22}H_{15}N_3O_2S$; 0.4 $H_2O$ | Requires | C 67.30 | H 4.06 | N 10.7 | S 8.17 |

EXAMPLE 2
5-(4-Hydroxyphenylsulphanyl)-2-amino-1H-indole-3-carbonitrile

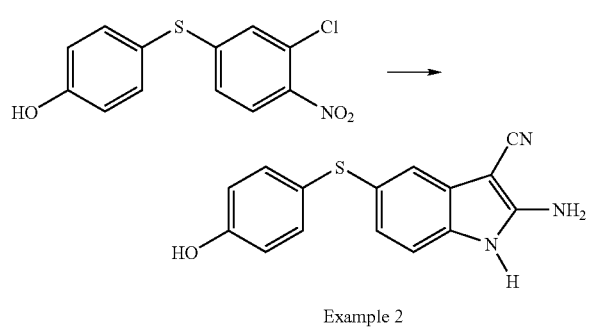

Example 2

A stirred solution of 4-(4-hydroxyphenylsulphanyl)-2-chloro-nitrobenzene (42 g; 150 mmol) and malononitrile (9.9 g; 150 mmol) in N-methyl-2-pyrrolidinone (150 ml) was treated dropwise with a 10 M aqueous solution of sodium hydroxide (45 ml; 450 mmol). The mixture was stirred at room temperature for 50 hours.

The mixture was diluted with DMF (300 ml) and a solution of $NaHCO_3$ (105 g; 1.25 mol) in water (420 ml) was added. To this solution was added sodium dithionite (74 g; 0.425 mol) followed by further solid $NaHCO_3$ (105 g) and sodium dithionite (74 g). The resulting suspension was well stirred at room temperature until the purple colouration had disappeared (at least one night). Mineral salts were filtered and the filtrate was poured into water (4 l). The mixture was extracted with EtOAc (2×) and the combined extracts washed well with water, then brine and dried over $MgSO_4$.

The residue was purified by flash chromatography eluting with increasingly polar mixtures of EtOAc/hexanes (60 to 75% EtOAc). The appropriate fractions were evaporated to give 5-(4-hydroxyphenylsulphanyl)-2-amino-1H-indole-3-carbonitrile as a beige solid (26.2 g).

Yield: 62%.

Further flash chromatography of a small sample eluting with increasingly polar mixtures of EtOAc/hexanes (60–70% EtOAc) gave colourless crystals, Melting Point 241–242° C.

$^1$H NMR spectrum (DMSO $d_6$): 6.76 (d, 2H); 6.85 (s, 2H); 6.87 (dd, 1H); 6.98 (d, 1H); 7.09 (d, 1H); 7.2 (d, 2H); 9.66 (br s, 1H); 10.79 (br s, 1H).

MS-ESI: 282 [MH]$^+$

| Elemental analysis: | Found | C 64.22 | H 4.19 | N 14.84 | S 11.11 |
|---|---|---|---|---|---|
| $C_{15}H_{11}N_3OS$ | Requires | C 64.04 | H 3.94 | N 14.94 | S 11.4 |

4-(4-Hydroxyphenylsulphanyl)-2-chloro-nitrobenzene was prepared as follows:

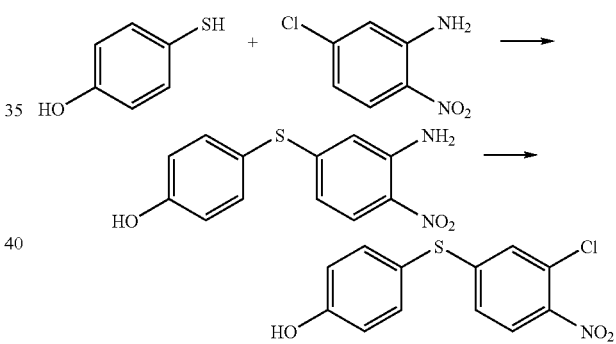

4-(4-Hydroxyphenylsulphanyl)-2-amino-nitrobenzene

A solution of 4-hydroxybenzenethiol (46 g; 328 mmol) in DMA (500 ml) under argon was cooled to 0° C. and treated portionwise with NaH (28.9 g; 722 mmol; 60 % dispersion in oil). The mixture was stirred at room temperature for 2 hours and then solid 4-chloro-2-amino-nitrobenzene (56.6 g; 328 mmol) was added rapidly portionwise. The mixture was stirred and heated at 80° C. for 30 minutes and allowed to cool overnight. The mixture was poured into aqueous HCl (2 N) and the precipitate was filtered, washed with water, then pentane and dried in vacuo to give 4-(4-hydroxyphenylsulphanyl)-2-amino-nitrobenzene as a beige solid (86.6 g).

Yield: 100%

Purification of a small sample by flash chromatography eluting with increasingly polar mixtures of EtOAc/hexanes (40 to 60% EtOAc) gave analytically pure 4-(4-hydroxyphenylsulphanyl)-2-amino-nitrobenzene as a white solid.

$^1$H NMR spectrum (DMSO $d_6$): 6.27 (dd, 1H); 6.5 (d, 1H); 6.92 (d, 2H); 7.41 (d, 2H); 7.44 (s, 1H); 7.86 (d, 1H); 10.08 (br s, 1H).

MS-ESI: 262 [M]$^+$

| Elemental analysis: | Found | C 54.83 | H 3.95 | N 10.52 | S 11.99 |
| $C_{21}H_{26}NO_8P$; 0.7 $H_2O$ | Requires | C 54.95 | H 3.84 | N 10.68 | S 12.22 |

4-(4-Hydroxyphenylsulphanyl)-2-chloro-nitrobenzene 4-(4-Hydroxyphenylsulphanyl)-2-amino-nitrobenzene (85.9 g; 327 mmol) was dissolved in a mixture of AcOH (1.0 l) and concentrated HCl (400 ml) by stirring and warming to 60° C. The cooled solution was added slowly to a mechanically stirred mixture of ice (1.6 kg) and concentrated HCl (400 ml) to obtain a fine suspension which was further stirred overnight. The suspension was cooled to 5° C. and a chilled solution of $NaNO_2$ (22.6 g; 327 mmol) in water (80 ml) was added dropwise, while maintaining the temperature of the mixture between 0° C. and 5° C. The mixture was stirred for a further 3 hours and was poured slowly into a solution of CuCl (32.3 g; 327 mmol) in a mixture of concentrated HCl (160 ml) and water (120 ml) at 35° C. After the addition was complete, the mixture was warmed at 50° C. for 1 hour and then allowed to cool.

The solid which separated was filtered and digested in EtOAc (4 l). The organic phase was washed with sat. aqueous $NaHCO_3$, then brine and dried over $MgSO_4$.

The residue (85 g) was purified by flash chromatography eluting with $CH_2Cl_2$. The appropriate fractions were evaporated to give 4-(4-hydroxyphenylsulphanyl)-2-chloro-nitrobenzene as a yellow solid (45.1 g).

Yield: 49%

$^1$H NMR spectrum ($CDCl_3$): 5.18 (s, 1H); 6.93–6.99 (m, 3H); 7.09 (d, 1H); 7.44 (d, 2H); 7.79 (d, 1H).

MS-ESI: 280 $[M-H]^-$

| Elemental analysis: | Found | C 51.1 | H 2.85 | N 5.03 | S 11.16 |
| $C_{12}H_8ClNO_3S$ | Requires | C 51.16 | H 2.86 | N 4.97 | S 11.38 |

EXAMPLE 3

5-(3,4-Dimethoxyphenylsulphanyl)-2-amino-1H-indole-3-carbonitrile

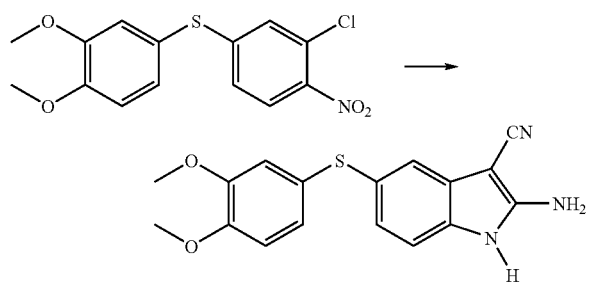

Example 3

Using the general method described for Example 2, except that two equivalents of aqueous NaOH were employed, 5-(3,4-dimethoxyphenylsulphanyl)-2-amino-1H-indole-3-carbonitrile was obtained from 4-(3,4-dimethoxyphenylsulphanyl)-2-chloro-nitrobenzene (1.7 g; 5.2 mmol) after purification by flash chromatography eluting with increasingly polar mixtures of EtOAc/hexanes (50 to 60% EtOAc). The product was a beige solid (745 mg), Melting Point 169–173° C.

Yield: 44%

$^1$H NMR spectrum (DMSO $d_6$): 3.71 (s, 3H); 3.75 (s, 3H); 6.82 (dd, 1H); 6.88 (s, 2H); 6.93 (m, 3H); 7.08 (d, 1H); 7.12 (d, 1H); 10.85 (br s, 1H).

MS-ESI: 325 $[M]^+$ 4-(3,4-Dimethoxyphenylsulphanyl)-2-chloro-nitrobenzene was prepared using the general method described for 4-(4-hydroxyphenylsulphanyl)-2-chloro-nitrobenzene in Example 2, except that one equivalent of NaH was used in the first step.

4-(3,4-Dimethoxyphenylsulphanyl)-2-amino-nitrobenzene

In the first step 4-(3,4-dimethoxyphenylsulphanyl)-2-amino-nitrobenzene was prepared (15.45 g):

Yield: 100%

$^1$H NMR spectrum (DMSO $d_6$): 3.78 (s, 3H); 3.82 (s, 3H); 6.31 (dd, 1H); 6.54 (d, 1H); 7.08–7.41 (m, 3H); 7.45 (s, 2H); 7.86 (d, 1H).

MS-ESI: 306 $[M]^+$

| Elemental analysis: | Found | C 54.57 | H 4.59 | N 9.15 | S 9.87 |
| $C_{14}H_{14}N_2O_4S$ | Requires | C 54.89 | H 4.61 | N 9.14 | S 10.47 |

4-(3,4-Dimethoxyphenylsulphanyl)-2-chloro-nitrobenzene

In the second step 4-(3,4-dimethoxyphenylsulphanyl)-2-chloro-nitrobenzene was prepared (2.27 g):

Yield: 56%

$^1$H NMR spectrum ($CDCl_3$): 3.89 (s, 3H); 3.95 (s, 3H); 6.85–6.99 (m, 2H); 7.02 (d, 1H); 7.11 (d, 1H); 7.17 (dd, 2H); 7.79 (d, 1H).

| Elemental analysis: | Found | C 51.45 | H 3.78 | N 4.38 | S 9.77 |
| $C_{14}H_{12}ClNO_4S$ | Requires | C 51.62 | H 3.71 | N 4.3 | S 9.84 |

EXAMPLE 4

5-(3-Methoxyphenylsulphanyl)-2-amino-1H-indole-3-carbonitrile

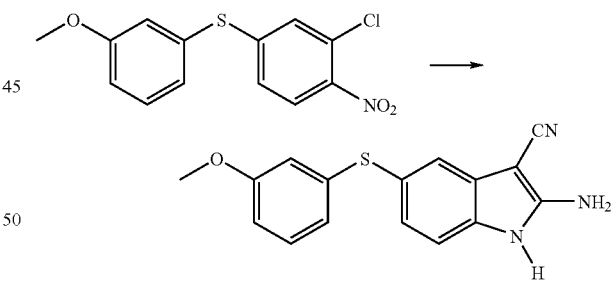

Example 4

This compound was prepared by the use of a Zymate (trade mark) Laboratory Automation System XP2 Robot (Zymark Corp.).

Thus, 4-(3-methoxyphenylsulphanyl)-2-chloro-nitrobenzene (2.45 g; 8.28 mmol) was introduced into a robot tube. A solution of malononitrile (2 M, 8.3 mmol) in N-methyl-2-pyrrolidinone was pumped into the tube and the mixture vortexed. Aqueous sodium hydroxide (10 M, 16.6 mmol) was pumped in and the mixture was then vortexed and stirred for 3 days at room temperature. The contents of the tube were divided equally into a further five tubes. To each was added DMF (3 ml), water (4 ml), $NaHCO_3$ (1 g), sodium dithionate (700 mg) followed by further NaHCO$_3$ (1 g) and sodium dithionate (700 mg) with vortexing between each addition. The mixture was stirred overnight at room temperature.

Each tube was diluted with water (4 ml) and extracted with EtOAc (2×7 ml). The organic phase was evaporated, the residues were combined in CH$_2$Cl$_2$, treated SiO$_2$ (5 g) and evaporated to dryness. The residue was purified by flash chromatography eluting automatically with CH$_2$Cl$_2$ and then EtOAc/CH$_2$Cl$_2$ (50/50). The appropriate fractions were evaporated, triturated with EtOAc/hexanes, filtered, rinsed and dried to give 5-3-methoxyphenylsulphanyl)-2-amino-1H-indole-3-carbonitrile as a cream solid (473 mg).

Yield: 19%

$^1$H NMR spectrum (DMSO d$_6$): 3.68 (s, 3H); 6.62–6.66 (m, 2H); 6.73 (dd, 1H); 6.95 (s, 2H); 7.05 (dd, 1H); 7.15–7.2 (m, 3H); 10.93 (br s, 1H).

MS-ESI: 296 [M]$^+$

All samples prepared by the Robot contained small quantities of DMF and N-methyl-2-pyrrolidinone and were not analysed for elemental composition.

The starting material was prepared as follows:

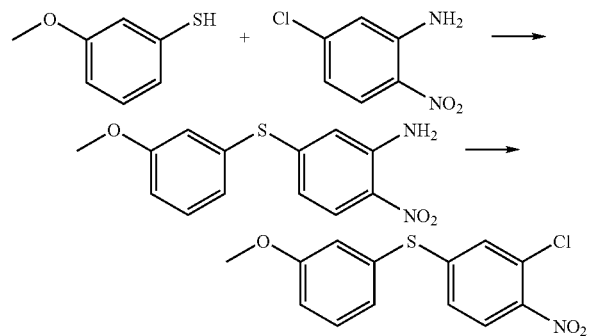

Using the general method described in Example 2, except that one equivalent of NaH was used in the first step, 3-methoxybenzenethiol (2.1 g; 15 mmol) was used to prepare:-

4-(3-Methoxyphenylsulphanyl)-2-amino-nitrobenzene (4.0 g):

Yield: 97%

$^1$H NMR spectrum (CDCl$_3$): 3.82 (s, 3H); 6.03 (br s, 2H); 6.39 (d, 1H); 6.45 (dd, 1H); 6.98 (dt, 1H); 7.06 (t, 1H); 7.13 (dt, 1H); 7.35 (t, 1H); 7.98 (d, 1H).

MS-ESI: 277 [MH]$^+$

And then:

4-(3-Methoxyphenylsulphanyl)-2-chloro-nitrobenzene (2.27 g):

Yield: 53%

$^1$H NMR spectrum (CDCl$_3$): 3.85 (s, 3H); 7.03 (dd, 1H); 7.07–7.1 (m, 2H); 7.14 (dd, 1H); 7.23 (d, 1H); 7.39 (t, 1H); 7.82 (d, 1H).

EXAMPLES 5–8

The examples in the following table were prepared using the Zymate (trade mark) Robot as described in Example 4, from the corresponding substituted 2-chloro-nitrobenzene.

| Example | R$^a$ | R$^b$ | Footnote |
|---|---|---|---|
| 5 | 4-fluorophenylsulphanyl | H | a |
| 6 | 2-naphthylsulphanyl | H | b |
| 7 | H | F | c |
| 8 | F | CH$_3$— | d |

Footnotes a Starting material: 4-(4-fluorophenylsulphanyl)-2-chloro-nitrobenzene 2.3 g 8.11 mmol Yield: 289 mg 13% $^1$H NMR spectrum (DMSO d$_6$): 6.94(s, 2H); 7.03(dd, 1H); 7.12–7.23(m, 6H); 10.91(brs, 1H). MS-ESI: 284 [MH]$^+$
b Starting material: 4-(2-naphthylsulphanyl)-2-chloro-nitrobenzene 1.7 g 5.4 mmol Yield: 366 mg 21% $^1$H NMR spectrum (DMSO d$_6$): 6.95(s, 2H); 7.08(dd, 1H); 7.2–7.27(m, 3H); 7.47(m, 2H); 7.65(s, 1H); 7.76(d, 1H); 7.84(t, 2H); 10.94(brs, 1H). MS-ESI: 314 [M − H]$^-$
c Starting material: 5-fluoro-2-chloro-nitrobenzene 1.75 g 9.97 mmol Yield: 18 mg 1% $^1$H NMR spectrum (DMSO d$_6$): 6.78(s, 2H); 6.79(ddd, 1H); 6.96(dd, 1H) 7.07(dd, 1H); 10.76(brs, 1H). MS-ESI: 175 [M]$^+$
d Starting material: 4-fluoro-5-methyl-2-chloro-nitrobenzene 1.89 g 9.97 mmol Yield: 53 mg 3% $^1$H NMR spectrum (DMSO d$_6$): 6.74(s, 2H); 6.81 (d, 1H); 6.96(d, 1H); 10.62(brs, 1H). MS-ESI: 188 [M − H]$^-$ Starting Materials—Example 5

Starting material 4-(4-fluorophenylsulphanyl)-2-chloro-nitrobenzene was prepared as described in Example 4.

4-(4-Fluorophenylsulphanyl)-2-amino-nitrobenzene:

Starting material: 4-fluorobenzenethiol 1.92 g 15 mmol

Yield: 3.69 g 93%

$^1$H NMR spectrum (CDCl$_3$): 6.03 (br s, 2H); 6.31 (d, 1H); 6.38 (dd, 1H); 7.15 (t, 2H); 7.54 (dd, 2H); 7.98 (d, 1H).

MS-ESI: 265 [MH]$^+$ 4-(4-Fluorophenylsulphanyl)-2-chloro-nitrobenzene:

Yield: 1.72 g 44%

$^1$H NMR spectrum (DMSO d$_6$): 7.0 (dd, 1H); 7.13–7.2 (m, 3H); 7.55 (m, 2H); 7.81 (d, 1H).

MS-EI: 283 [M]$^+$

Starting Materials—Example 6

Starting material 4-(2-naphthylsulphanyl)-2-chloro-nitrobenzene was prepared as described in Example 4.

4-(2-Naphthylsulphanyl)-2-amino-nitrobenzene:

Starting material: naphthalene-2-thiol 2.4 g 15 mmol

Yield: 4.45 g 100%

$^1$H NMR spectrum (DMSO d$_6$): 6.40 (dd, 1H); 6.66 (s, 1H); 7.43 (br s, 2H); 7.54 (dd, 1H); 7.63 (m, 2H); 7.89 (d, 1H); 8.03 (m, 3H); 8.24 (s, 1H).

MS-ESI: 295 [M−H]$^-$ 4-(2-Naphthylsulphanyl)-2-chloro-nitrobenzene:

Yield: 1.75 g 37%

$^1$H NMR spectrum (CDCl$_3$): 7.07 (dd, 1H); 7.23 (d, 1H); 7.5 (dd, 1H); 7.59 (m, 2H); 7.79 (d, 1H); 7.83–7.93 (m, 3H); 8.1 (s, 1H).

MS-EI: 315 [M]$^+$

Starting Materials—Examples 7 and 8

Starting materials 5-fluoro-2-chloro-nitrobenzene and 5-methyl-4-fluoro-2-chloro-nitrobenzene are commercially available.

EXAMPLE 9
5-(4-Methoxyphenoxy)-2-amino-1H-indole-3-carbonitrile

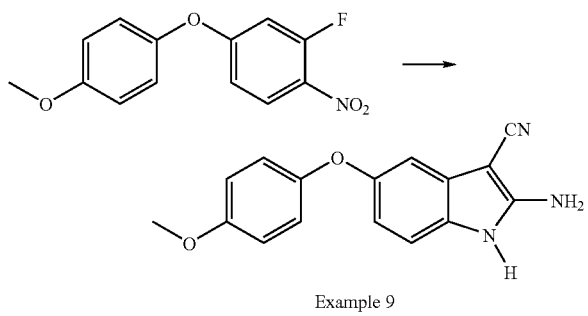

Example 9

Using the general method described for Example 2, Example 9 was prepared from a 1:2 mixture of 4-(4-methoxyphenoxy)-2-fluoro-nitrobenzene (a) and its isomer 2-(4-methoxyphenoxy)-4-fluoro-nitrobenzene was used (b) (see below) (5.97 g; 22.7 mmol), except that two equivalents of aqueous NaOH were employed, after purification by flash chromatography eluting with increasingly polar mixtures of EtOAc/hexanes (40 to 100% EtOAc), 5-(4-methoxyphenoxy)-2-amino-1H-indole-3-carbonitrile was obtained as a light beige solid (1.32 g), Melting Point 216–217° C.

Yield: 21%

$^1$H NMR spectrum (DMSO $d_6$): 3.75 (s, 3H); 6.58 (dd, 1H); 6.63 (d, 1H); 6.80 (s, 2H); 6.93 (s, 4H); 7.09 (d, 1H); 10.69 (br s, 1H).

MS-ESI: 278 [M–H]$^-$

| Elemental analysis: | Found | C 65.78 | H 4.52 | N 14.68 |
|---|---|---|---|---|
| $C_{16}H_{13}N_3O_2$; 0.7 $H_2O$ | Requires | C 65.83 | H 4.97 | N 14.39 |

The 1:2 mixture of 4-(4-methoxyphenoxy)-2-fluoronitrobenzene (a) and its isomer 2-(4-methoxyphenoxy)-4-fluoronitrobenzene (b) was prepared as follows:

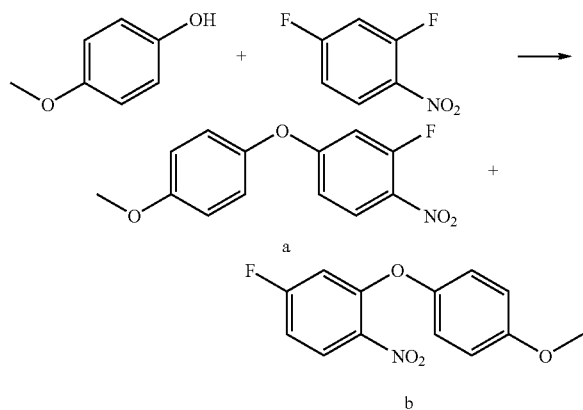

A solution of 4-methoxyphenol (3.75 g; 30 mmol) in DMA (40 ml) under argon was cooled to 0° C. and treated portionwise with NaH (1.35 g; 33 mmol ; 60% dispersion in oil). The mixture was stirred at room temperature for 1 hour. This mixture was added dropwise to a solution of 2,4-difluoro-nitrobenzene(3.3 ml; 30 mmol) in DMA (10 ml) over 1 hour. The mixture was allowed to stir overnight and was then poured into aqueous HCl (10%) and extracted with Et$_2$O (3×). The organic phase was washed with water, then brine, and dried over MgSO$_4$.

The residue (9.14 g) was purified by flash chromatography eluting with increasingly polar mixtures of EtOAc/hexanes (0 to 20% EtOAc). The appropriate fractions were evaporated to give a mixture of 4-(4-methoxyphenoxy)-2-fluoronitrobenzene (a) and its isomer 2-(4-methoxyphenoxy)-4-fluoronitrobenzene (b) (5.97 g; 1:2 as determined by $^1$H NMR).

Yield: 76%

$^1$H NMR spectrum (CDCl$_3$): 3.83 (s, 3H, b); 3.84 (s, 3H, a); 6.56 (dd, 1H, b); 6.71 (dd, 1H, a); 6.76–6.82 (m, 1H, b and 1H, a); 6.94–6.97 (m, 2H, b and 2H, a); 7.02–7.06 (m, 2H, b and 2H, a); 8.02 (dd, 1H, b); 8.07 (dd, 1H, a).

EXAMPLE 10
5-(3,6-Dimethoxyphenylsulphanyl)-2-amino-1H-indole-3-carbonitrile

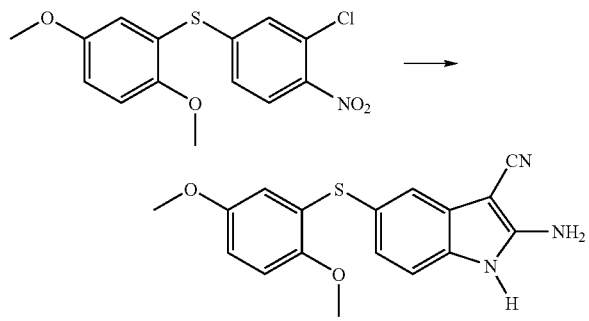

Example 10

5-(3,6-Dimethoxyphenylsulphanyl)-2-amino-1H-indole-3-carbonitrile (1.22 g) was prepared using the general method described in Example 2, except that two equivalents of aqueous NaOH were employed, it was obtained as a white solid from 4-(3,6-dimethoxyphenylsulphanyl)-2-chloronitrobenzene (2.1 g; 6.45 mmol) after purification by flash chromatography eluting with increasingly polar mixtures of CH$_2$Cl$_2$/EtOAc (0 to 50% EtOAc).

Yield: 58%

$^1$H NMR spectrum (DMSO $d_6$): 3.54 (s, 3H); 3.80 (s, 3H); 6.08 (d, 1H); 6.68 (dd, 1H); 6.93 (d, 1H); 6.98 (s, 2H); 7.05 (dd, 1H); 7.20 (d, 1H); 7.24 (d, 1H); 10.98 (br s, 1H).

LCMS-ESI: 326 [M+H]$^+$

| Elemental analysis: | Found | C 61.8 | H 5.07 | N 12.1 | S 8.78 |
|---|---|---|---|---|---|
| $C_{17}H_{15}N_3O_2S$; 0.35 EtOAc | Requires | C 62.04 | H 5.04 | N 11.8 | S 9.0 |

4-(3.6-Dimethoxyphenylsulphanyl)-2-amino-nitrobenzene

Using the general method described for 4-(4-hydroxyphenylsulphanyl)-2-amino-nitrobenzene in Example 2, except that one equivalent of NaH was used, 4-(3,6-dimethoxyphenylsulphanyl)-2-amino-nitrobenzene (4.19 g) was prepared from 3,6-dimethoxybenzenethiol (2.55 g; 15 mmol).

Yield: 91%

$^1$H NMR spectrum (CDCl$_3$): 3.78 (s, 3H); 3.79 (s, 3H); 6.02 (s, 2H); 6.37 (d, 1H); 6.41 (dd, 1H); 6.90–7.07 (m, 3H); 7.96 (d, 1H).

MS-ESI: 307 [M+H]$^+$ 4-(3,6-dimethoxyphenylsulphanyl)-2-chloro-nitrobenzene

Similarly, using the general method described for 4-(4-hydroxyphenylsulphanyl)-2-chloro-nitrobenzene in Example 2, 4-(3,6-dimethoxyphenylsulphanyl)-2-chloro-nitrobenzene (2.22 g) was prepared from 4-(3,6-dimethoxyphenylsulphanyl)-2-amino-nitrobenzene (4.15 g; 15 mmol) after purification by flash chromatography eluting with increasingly polar mixtures of EtOAc/hexanes (10 to 20% EtOAc).

Yield: 50%

$^1$H NMR spectrum (CDCl$_3$): 3.78 (s, 3H); 3.79 (s, 3H); 6.96 (d, 1H); 7.02 (m, 2H); 7.08 (d, 1H); 7.15 (d, 2H); 7.79 (d, 1H).

MS-ESI: 326 [M]$^+$

EXAMPLE 11

5-(3,4,5-Trimethoxyphenoxy)-2-amino-1H-indole-3-carbonitrile

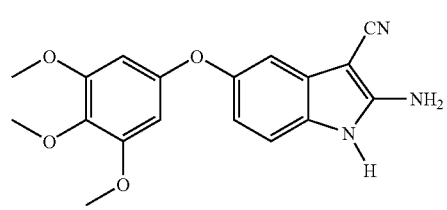

Example 11

5-(3,4,5-Trimethoxyphenoxy)-2-amino-1H-indole-3-carbonitrile (1.49 g) was prepared using the general method described in Example 2, except that two equivalents of aqueous NaOH were employed, it was obtained as a beige solid, melting point 208–209° C., from a 1:2 mixture of 4-(3,4,5-trimethoxyphenoxy)-2-fluoro-nitrobenzene (c) and its isomer 2-(3,4,5-trimethoxyphenoxy)-4-fluoro-nitrobenzene (d) (8.01 g; 25 mmol; present in a 1:2 mixture of isomers) after purification by flash chromatography eluting with increasingly polar mixtures of EtOAc/hexanes (40 to 100% EtOAc).

Yield: 18%

$^1$H NMR spectrum (DMSO d$_6$): 3.64 (s, 3H); 3.70 (s, 6H); 6.28 (s, 2H); 6.64 (dd, 1H); 6.74 (s, 1H); 6.83 (s, 2H); 7.13 (d, 1H); 10.72 (br s, 1H).

LCMS-ESI: 340 [M+H]$^+$

| Elemental analysis: | Found | C 62.66 | H 5.12 | N 12.22 |
|---|---|---|---|---|
| C$_{18}$H$_{17}$N$_3$O$_4$; 0.3 H$_2$O | Requires | C 62.71 | H 5.15 | N 12.19 |

The starting material was prepared as follows:

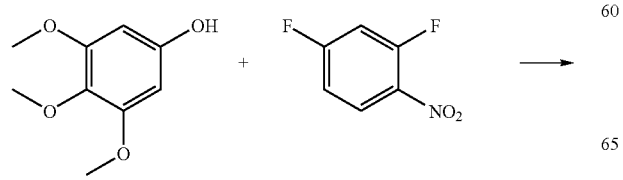

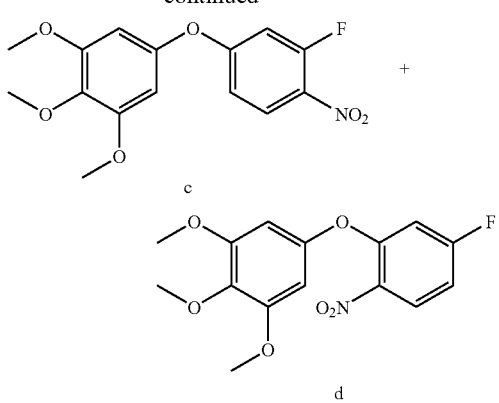

Using the general method described in Example 9, a mixture of 4-(3,4,5-trimethoxyphenoxy)-2-fluoro-nitrobenzene (c) and its isomer 2-(3,4,5-trimethoxyphenoxy)-4-fluoro-nitrobenzene (d) (8.01 g; proportions of b/bi 1:2 as determined by $^1$H NMR) was obtained from 3,4,5-trimethoxyphenol (5.52 g; 30 mmol) after purification by flash chromatography eluting with increasingly polar mixtures of EtOAc/hexanes (0 to 50% EtOAc).

Yield: 83%

$^1$H NMR spectrum (CDCl$_3$): 3.8–3.84 (m, 9H, c and 9H, d); 6.31 (s, 2H, c); 6.33 (s, 2H, d); 6.63 (dd, 1H, d); 6.75 (dd, 1H, c); 6.77–6.84 (m, 1H, c and 1H, d); 7.99–8.09 (m, 1H, c and 1H, d).

EXAMPLES 12 AND EXAMPLE 13

5-Phenylsulphanyl-2-(4-methylpiperazin-1-ylpropoxycarbonylamino)-1H-indole-3-carbonitrile, and 5-Phenylsulphanyl-1-(4-methylpiperazin-1-ylpropoxycarbonyl)-2-amino-1H-indole-3-carbonitrile respectively

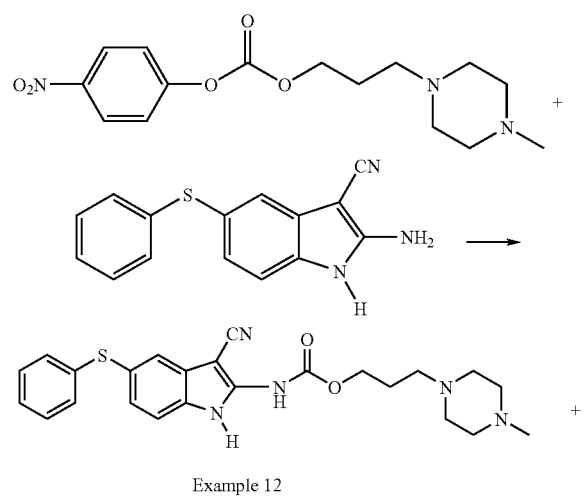

Example 12

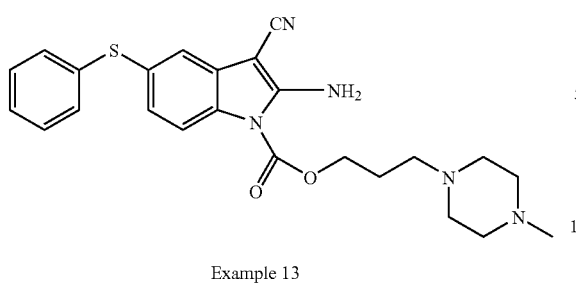

Example 13

A solution of 5-phenylsulphanyl-2-amino-1H-indole-3-carbonitrile (265 mg; 1.0 mmol) in DMF (40 ml) under argon at room temperature was treated portionwise with NaH (200 g; 5 mmol; 60% dispersion in oil). The mixture was stirred at room temperature for 30 minutes and 3-(4-methylpiperazin-1-yl)propyl 4-nitrophenyl carbonate (627 mg; 1.5 mmol) was added portionwise. The mixture was stirred for 1 hour, poured into water and extracted with EtOAc. The organic phase was washed with $H_2O$, brine and dried over $MgSO_4$. The residue was triturated with $Et_2O$ to give 5-phenylsulphanyl-1-(4-methylpiperazin-1-ylpropoxycarbonyl)-2-amino-1H-indole-3-carbonitrile as a beige solid (162 mg).

Yield: 36%

$^1$H NMR spectrum (DMSO $d_6$): 1.95 (t, 2H); 2.05 (s, 3H); 2.05–2.55 (m, 10H); 4.52 (t, 2H); 7.11 (m, 2H); 7.26 (m, 3H); 7.34 (m, 2H); 7.82 (d, 1H); 7.89 (s, 2H).

LCMS-ESI: 450 [M+H]$^+$

| Elemental analysis | Found | C 53.93 | H 5.48 | N 13.10 | S 5.55 |
|---|---|---|---|---|---|
| $C_{24}H_{27}N_5O_2S$; 2.35 HCl | Requires | C 53.86 | H 5.53 | N 13.08 | S 5.99 |

The filtrate was purified by flash chromatography eluting with MeOH/$CH_2Cl_2$ (10% MeOH) and the appropriate fractions were evaporated to give 5-phenylsulphanyl-2-(4-methylpiperazin-1-ylpropoxycarbonylamino)-1H-indole-3-carbonitrile (40 mg).

Yield: 9%

$^1$H NMR spectrum (DMSO $d_6$): 1.81 (t, 2H); 2.15 (s, 3H); 2.2–2.25 (m, 10H); 4.21 (t, 2H); 7.16–7.25 (m, 4H); 7.3 (m, 2H); 7.46 (d, 1H); 7.55 (d, 1H); 11.2 (br s, 1H); 12.1 (br s, 1H).

LCMS-ESI: 450 [M+H]$^+$

| Elemental analysis: | Found | C 62.04 | H 5.99 | N 14.30 | S 5.98 |
|---|---|---|---|---|---|
| $C_{24}H_{27}N_5O_2S$; 0.4 HCl 0.2 EtOAc | Requires | C 61.83 | H 6.07 | N 14.54 | S 6.66 |

3-(4-Methylpiperazin-1-yl)-propyl-4-nitrophenyl carbonate
This starting material was prepared as follows:

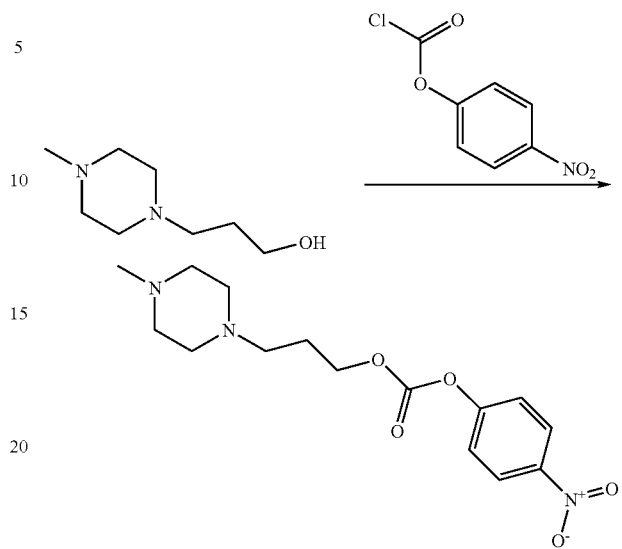

4-Nitrophenyl chloroformate (636 mg; 3.16 mmol) was added to a solution of 3-(4-methylpiperazin-1-yl) propanol [Synthesis (1997),6, 643–648] (500 mg; 3.16 mmol) and triethylamine (440 ul; 3.16 mmol) in dichloromethane (20 ml) under argon atmosphere at 0° C. The mixture was stirred at ambient temperature for 3 hours, evaporated to dryness and triturated with $Et_2O$/aq. HCl (2 N). The precipitate was filtered, washed with $Et_2O$ and dried to give the dihydrochloride of 3-(4-methylpiperazin-1-yl)-propyl 4-nitrophenyl carbonate (1.22 g).

Yield: 98%.

$^1$H NMR (DMSO $d_6$): 2.16 (m, 2H); 2.81 (s, 3H); 3.1–3.8 (m, 10H); 4.33 (t, 2H); 7.57 (d, 2H); 8.31 (d, 2H).

EXAMPLE 14

5-(4-Acetylaminophenoxy)-2-amino-1H-indole-3-carbonitrile

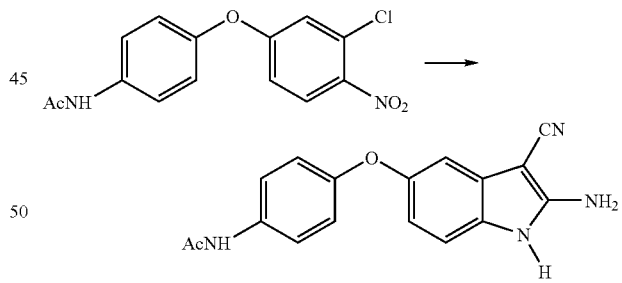

Example 14

5-(4-Acetylaminophenoxy)-2-amino-1H-indole-3-carbonitrile (4.82 g) was prepared using the general method described in Example 2, except that two equivalents of aqueous NaOH were employed, it was obtained as a beige solid from 4-(4-acetylaminophenoxy)-2-chloronitrobenzene (6.13 g; 20 mmol) after purification by trituration with a mixture of EtOAc/$CH_2Cl_2$.

Yield: 79%

$^1$H NMR spectrum (DMSO $d_6$): 2.02 (s, 3H); 6.59 (dd, 1H); 6.66 (d, 1H); 6.79 (s, 2H); 6.89 (d, 2H); 7.10 (d, 1H); 7.53 (d, 2H); 9.88 (s, 1H); 10.69 (br s, 1H).

LCMS-ESI: 307 [M+H]$^+$

| Elemental analysis: | Found | C 66.39 | H 4.77 | N 17.67 |
| $C_{17}H_{14}N_4O_2$ 0.1 EtOAc | Requires | C 66.32 | H 4.73 | N 17.78 |

The starting material was prepared as follows:
4-(4-Acetylaminophenoxy)-2-amino-nitrobenzene 4-(4-Acetylaminophenoxy)-2-amino-nitrobenzene (46.57 g) was prepared from 4-acetylaminophenol (30.2 g; 0.2 mol) using the general method described for 4-(4-hydroxyphenylsulphanyl)-2-amino-nitrobenzene in Example 2, except that one equivalent of NaH was used.

Yield: 81%

$^1$H NMR spectrum (DMSO $d_6$): 2.07 (s, 3H); 6.3 (m, 2H); 7.12 (d, 2H); 7.48 (s, 2H); 7.68 (d, 2H); 8.01 (d, 1H); 10.06 (s, 1H).

4-(4-Acetylaminophenoxy)-2-chloro-nitrobenzene

Similarly, using the general method described for 4-(4-hydroxyphenylsulphanyl)-2-chloro-nitrobenzene in Example 2, 4-(4-acetylaminophenoxy)-2-chloro-nitrobenzene (11.05 g) was prepared from 4-(4-acetylaminophenoxy)-2-amino-nitrobenzene (14.35 g; 0.5 mol) after purification by flash chromatography eluting with increasingly polar mixtures of EtOAc/hexanes (60 to 100% EtOAc).

Yield: 72%

$^1$H NMR spectrum (DMSO $d_6$): 2.07 (s, 3H); 7.05 (dd, 1H); 7.17 (d, 2H); 7.27 (d, 1H); 7.70 (d, 2H); 8.14 (d, 1H); 10.09 (s, 1H).

LCMS-ESI: 307 [M+H]$^+$

EXAMPLE 15

5-(4-Aminophenoxy)-2-amino-1H-indole-3-carbonitrile

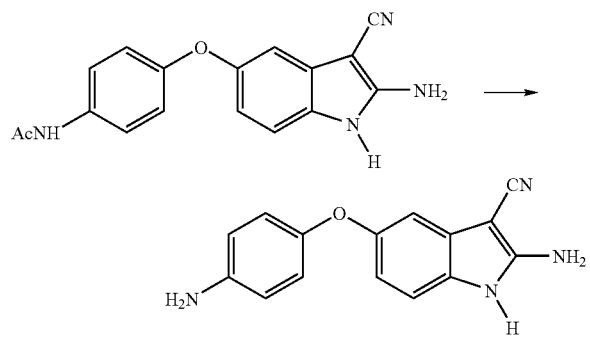

Example 15

A suspension of 5-(4-acetylaminophenoxy)-2-amino-1H-indole-3-carbonitrile (Example 14)(306 mg; 1 mmol) in MeOH (10 ml) was treated with water (2 ml) and conc. HCl (1 ml) and the mixture heated under reflux for 30 hours. After cooling the mixture was poured into sat. aqueous NaHCO$_3$ and extracted with EtOAc. The organic phase was washed with brine and dried over MgSO$_4$. The residue was purified by flash chromatography eluting with increasingly polar mixtures of EtOAc/hexanes (80 to 100% EtOAc) to give 5-(4-aminophenoxy)-2-amino-1H-indole-3-carbonitrile as a pale beige solid (251 mg).

Yield: 95%

$^1$H NMR spectrum (DMSO $d_6$): 4.89 (s, 2H); 6.55 (m, 4H); 6.73 (m, 4H); 7.06 (d, 1H); 10.61 (br s, 1H).

LCMS-ESI: 265 [M+H]$^+$

| Elemental analysis: | Found | C 67.40 | H 4.72 | N 20.38 |
| $C_{15}H_{12}N_4O$; 0.1 $H_2O$ 0.1 EtOAc | Requires | C 67.29 | H 4.77 | N 20.38 |

EXAMPLE 16

5-(4-Glycylaminophenoxy)-2-amino-1H-indole-3-carbonitrile

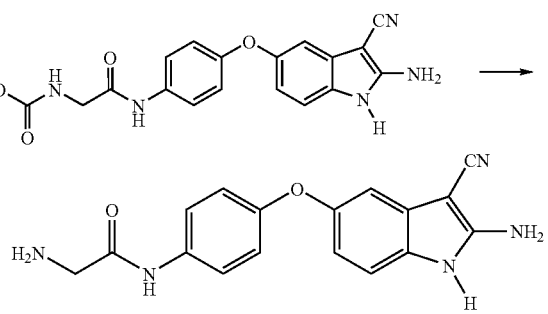

Example 16

A solution of 5-[4-({N-benzyoxycarbonylglycyl}amino)phenoxy]-2-amino-1H-indole-3-carbonitrile (368 mg; 0.8 mmol) in EtOAc (10 ml) and MeOH (10 ml) was hydrogenated over Pd/C (100 mg) at 1 Atmosphere at room temperature for 1 hour. After filtration and evaporation to dryness, the residue was purified by flash chromatography eluting with MeOH/CH$_2$Cl$_2$(10% MeOH) and the appropriate fractions were evaporated to give 5-(4-glycylaminophenoxy)-2-amino-1H-indole-3-carbonitrile (163 mg).

Yield: 63%

$^1$H NMR spectrum (DMSO $d_6$): 2.03 (s, 2H); 3.24 (m, 2H); 6.59 (dd, 1H); 6.66 (d, 1H); 6.79 (s, 2H); 6.91 (d, 2H); 7.10 (d, 1H); 7.59 (d, 2H); 9.72 (br s, 1H); 10.69 (br s, 1H).

LCMS-ESI: 322 [M+H]$^+$

| Elemental analysis: | Found | C 62.29 | H 5.03 | N 20.38 |
| $C_{17}H_{15}N_5O_2$; 0.2 $H_2O$ 0.2 MeOH | Requires | C 62.35 | H 4.93 | N 21.14 |

5-[4-({N-Benzyoxycarbonylglycyl}amino)phenoxy]-2-amino-1H-indole-3-carbonitrile

This was prepared as follows:

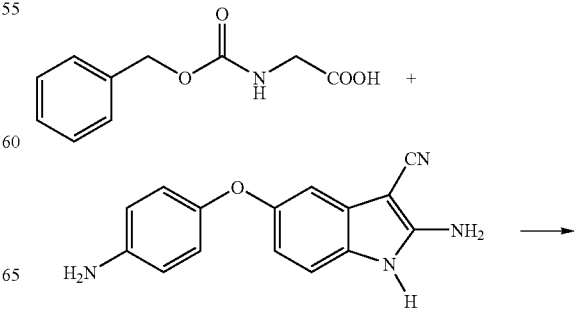

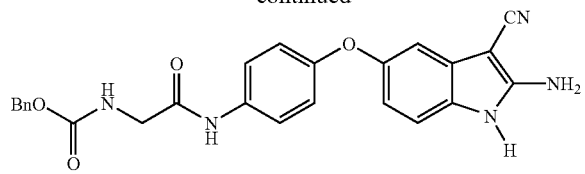

A solution of carbobenzyloxyglycine (480 mg; 2.26 mmol) and 5-(4-aminopbenoxy)-2-amino-1H-indole-3-carbonitrile (Example 15) (300 mg; 1.13 mmol) in CH$_2$Cl$_2$ (10 ml) was treated at room temperature with EDCI (546 mg; 2.8 mmol) and a catalytic quantity of DMAP (20 mg). The mixture was stirred for 1 hour and was directly purified by flash chromatography eluting with CH$_2$Cl$_2$/EtOAc (50/50). The appropriate fractions were evaporated to give 5-[4-({N-benzyoxycarbonylglycyl}amino)phenoxy]-2-amino-1H-indole-3-carbonitrile as a white solid (425 mg).

Yield: 83%

$^1$H NMR spectrum (DMSO d$_6$): 3.79 (d, 2H); 5.05 (s, 2H); 6.59 (dd, 1H); 6.67 (d, 1H); 6.80 (s, 2H); 6.91 (d, 2H); 7.10 (d, 1H); 7.2–7.45 (m, 5H); 7.5–7.6 (m, 3H); 9.92 (s, 1H); 10.69 (s, 1H).

LCMS-ESI: 454 [M–H]$^-$

EXAMPLE 17

5-(4-Alanylaminophenoxy)-2-amino-1H-indole-3-carbonitrile

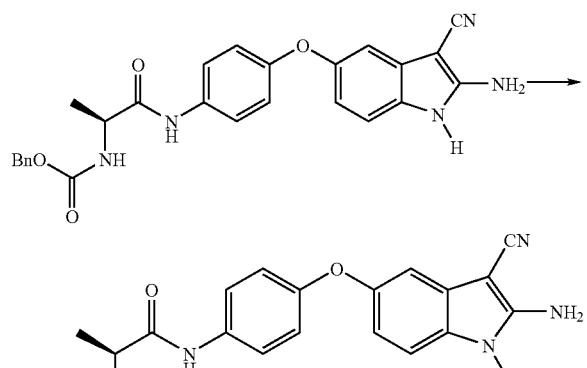

Example 17

Using the general method of hydrogenolysis described in Example 16, 5-(4-alanylaminophenoxy)-2-amino-1H-indole-3-carbonitrile (213 mg) was obtained as a white solid from 5-[4-({N-benzyloxycarbonylalanyl}amino)phenoxy]-2-amino-1H-indole-3-carbonitrile (514 mg; 1.1 mmol) after purification by flash chromatography eluting with MeOH/CH$_2$Cl$_2$ (10% MeOH).

Yield: 58%

$^1$H NMR spectrum (DMSO d$_6$): 1.20 (d, 3H); 1.98 (m, 2H); 3.40 (q, 1H); 6.59 (dd, 1H); 6.65 (d, 1H); 6.80 (s, 2H); 6.90 (m, 2H); 7.09 (d, 1H); 7.59 (m, 2H); 9.7 (br s, 1H); 10.6 (br s, 1H).

LCMS-ESI: 336 [M+H]$^+$

| Elemental analysis: | Found | C 63.79 | H 5.21 | N 20.52 |
|---|---|---|---|---|
| C$_{18}$H$_{17}$N$_5$O$_2$; 0.1 H$_2$O 0.1 MeOH | Requires | C 63.87 | H 5.21 | N 20.58 |

5-[4-({N-Benzyloxycarbonylalanyl}amino)phenoxy]-2-amino-1H-indole-3-carbonitrile This was prepared using the general coupling method described in Example 16, 5-[4-({N-benzyloxycarbonylalanyl}amino)phenoxy]-2-amino-1H-indole-3-carbonitrile (514 mg) was obtained as a white solid from 5-(4-aminophenoxy)-2-amino-1H-indole-3-carbonitrile (Example 15)(400 mg; 1.51 mmol) after purification by flash chromatography eluting with EtOAc/CH$_2$Cl$_2$ (50/50).

Yield: 72%

$^1$H NMR spectrum (DMSO d$_6$): 1.29 (d, 3H); 4.18 (m, 1H); 5.03 (d, 2H); 6.58 (dd, 1H); 6.67 (d, 1H); 6.80 (s, 2H); 6.91 (d, 2H); 7.10 (d, 1H); 7.25–7.45 (m, 5H); 7.5–7.6 (m, 3H); 9.94 (s, 1H); 10.71 (s, 1H).

EXAMPLE 18

5-(4-α-Glutamylaminophenoxy)-2-amino-1H-indole-3-carbonitrile

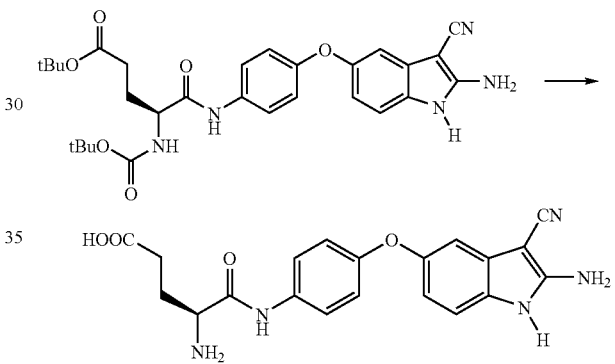

Example 18

A suspension of a tertiary butoxycarbonyl protected derivative of 5-(4-α-glutamylaminophenoxy)-2-amino-1H-indole-3-carbonitrile (1.21 g; 2.2 mmol) in CH$_2$Cl$_2$ (100 ml) was treated with a rapid stream of gaseous HCl for 2 hours at room temperature. The mixture was evaporated to dryness, taken up in water, filtered and the filtrate freeze-dried to give the hydrochloride salt of 5-(4-α-glutamylaminophenoxy)-2-amino-1H-indole-3-carbonitrile as a white powder (975 mg).

Yield: 100%

$^1$H NMR spectrum (DMSO d$_6$): 2.0–2.15 (m, 2H); 2.40 (m, 2H); 3.8 (br s, 1H); 4.04 (m, 1H); 6.60 (dd, 1H); 6.69 (d, 1H); 6.75 (br s, 1H); 6.95 (d, 2H); 7.12 (d, 1H); 7.59 (d, 2H) ; 8.43 (m, 3H); 10.79 (br s, 1H); 10.81 (br s, 1H) 12.2 (br s, 1H).

LCMS-ESI: 394 [M+H]$^+$

| Elemental analysis: | Found | C 52.88 | H 4.83 | N 15.06 | Cl 8.97 |
|---|---|---|---|---|---|
| C$_{17}$H$_{15}$N$_3$O$_2$S; 1.0 H$_2$O 1.15 HCl | Requires | C 52.97 | H 4.93 | N 15.44 | Cl 8.99 |

The tertiary butoxycarbonyl protected derivative of 5-(4-α-glutamylaminophenoxy)-2-amino-1H-indole-3- carbonitrile (1.49 g) was prepared using the general coupling method described in

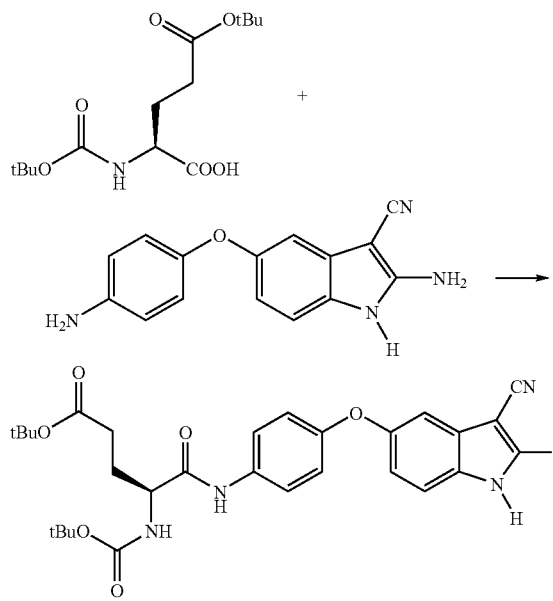

Example 16, as a white solid from 5-(4-aminophenoxy)-2-amino-1H-indole-3-carbonitrile (Example 15) (800 mg; 3.00 mmol) after purification by flash chromatography eluting with increasingly polar mixtures of EtOAc/hexanes (70 to 100% EtOAc).

Yield: 91%

$^1$H NMR spectrum (DMSO $d_6$): 1.38 (s, 18H); 1.80 (m, 1H); 1.90 (m, 1H); 2.26 (m, 2H); 4.05 (m, 1H); 6.59 (dd, 1H); 6.68 (d, 1H); 6.80 (s, 2H); 6.91 (d, 2H); 7.01 (d, 1H); 7.10 (d, 1H); 7.56 (d, 2H); 9.91 (s, 1H); 10.69 (s, 1H).

MS-ESI: 548 [M−H]$^-$

EXAMPLE 19

5-(4-Serylaminophenoxy)-2-amino-1H-indole-3-carbonitrile

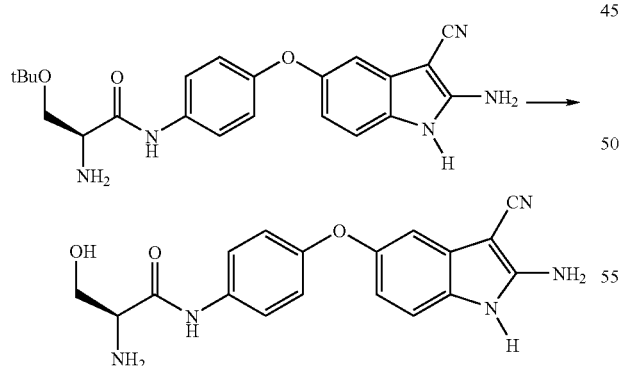

Example 19

Using the general method of deprotection described in Example 18, 5-(4-serylaminophenoxy)-2-amino-1H-indole-3-carbonitrile (554 mg) was obtained as its hydrochloride as a white solid from 5-[4-(O-t-butoxycarbonylserylamino) phenoxy]-2-amino-1H-indole-3-carbonitrile (800 mg; 2.0 mmol) after trituration with water, filtration and drying.

Yield: 73%

$^1$H NMR spectrum (DMSO $d_6$): 3.87 (m, 2H); 4.03 (m, 1H); 5.58 (m, 1H); 6.61 (dd, 1H); 6.68 (d, 1H); 6.85 (s, 2H); 6.96 (d, 2H); 7.13 (d, 1H); 7.62 (d, 2H); 8.31 (br s, 3H); 10.69 (s, 1H); 10.82 (s, 1H).

LCMS-ESI: 352 [M+H]$^+$

| Elemental analysis: | Found | C 53.55 | H 4.87 | N 17.27 |
|---|---|---|---|---|
| $C_{18}H_{17}N_5O_3$; 1.4 HCl | Requires | C 53.73 | H 4.61 | N 17.40 |

5-[4-(O-t-Butyloxycarbonylserylamino)phenoxy]-2-amino-1H-indole-3-carbonitrile was prepared as follows:

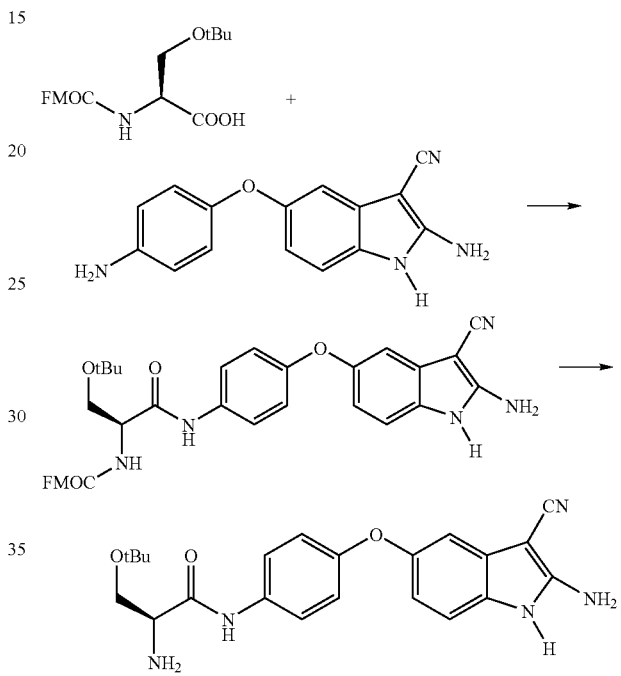

5-[4-({N-FMOC-O-t-butoxycarbonylseryl}amino)phenoxyl-2-amino-1H-indole-3-carbonitrile Using the general coupling method described in Example 16, 5-[4-({N-FMOC-O-t-butoxycarbonylseryl}amino)phenoxy]-2-amino-1H-indole-3-carbonitrile (1.68 g) was obtained as a white solid from 5-(4-aminophenoxy)-2-amino-1H-indole-3-carbonitrile (Example 15)(800 mg; 3.00 mmol) after purification by flash chromatography eluting with increasingly polar mixtures of EtOAc/hexanes (70 to 100% EtOAc).

Yield: 89%

$^1$H NMR spectrum (DMSO $d_6$): 1.12 (s, 9H); 3.55 (m, 2H); 4.15–4.35 (m, 4H); 6.59 (dd, 1H); 6.69 (d, 1H); 6.80 (s, 2H); 6.92 (d, 2H); 7.11 (d, 1H); 7.33 (m, 2H); 7.42 (m, 2H); 7.5–7.7 (m, 3H); 7.75 (m, 2H); 7.89 (d, 2H); 9.98 (s, 1H); 10.70 (s, 1H).

MS-ESI: 630 [M+H]$^+$

5-[4-(O-t-Butyloxycarbonylserylamino)phenoxy]-2-amino-1H-indole-3-carbonitrile

A solution of 5-[4-({N-FMOC-O-t-butoxycarbonylseryl}amino)phenoxy]-2-amino-1H-indole-3-carbonitrile (1.45 g; 2.3 mmol) in CHCl$_3$, (30 ml) was treated dropwise with piperidine (3.25 ml). The mixture was stirred for 3 hours at room temperature and was directly purified by flash chromatography eluting with increasingly polar mixtures of MeOH/CH$_2$Cl$_2$ (2.5 to 10% MeOH). The appropriate fractions were evaporated to give 5-[4-(O-t- butoxycarbonylserylamino)phenoxy]-2-amino-1H-indole-3-carbonitrile as a white solid (878 mg).

Yield: 94%

$^1$H NMR spectrum (DMSO d$_6$): 1.34 (s, 9H); 1.93 (br s, 2H); 3.4–3.55 (m, 3H); 6.61 (dd, 1H); 6.69 (d, 1H); 6.82 (s, 2H); 6.92 (d, 2H); 7.12 (d, 1H); 7.62 (d, 2H); 9.83 (br s, 1H); 10.73 (br s, 1H).

MS-ESI: 408 [M+H]$^+$

EXAMPLE 20

6-Benzyloxy-2-amino-1H-indole-3-carbonitrile

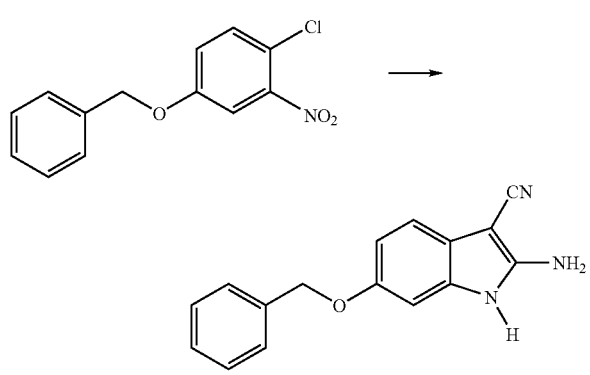

Example 20

Using the general method described in Example 2, except that two equivalents of aqueous NaOH were employed and the reaction was warmed to 100° C. in the first step, 6-benzyloxy-2-amino-1H-indole-3-carbonitrile (110 mg) was obtained as a beige solid from 5-benzyloxy-2-chloro-nitrobenzene (1.31 g; 5.0 mmol) after purification by flash chromatography eluting with increasingly polar mixtures of EtOAc/hexanes (30 to 70% EtOAc).

Yield: 8%

$^1$H NMR spectrum (DMSO d$_6$): 5.05 (s, 2H); 6.59 (s, 2H); 6.70 (dd, 1H); 6.82 (d, 1H); 7.01 (d, 1H); 7.31 (t, 1H); 7.38 (t, 2H); 7.44 (d, 2H); 10.56 (s, 1H).

LCMS-ESI: 264 [M+H]$^+$

| Elemental analysis: | Found | C 72.11 | H 4.91 | N 15.84 |
|---|---|---|---|---|
| C$_{16}$H$_{13}$N$_3$O; 0.2 H$_2$O | Requires | C 72.0 | H 5.06 | N 15.74 |

5-Benzyloxy-2-chloro-nitrobenzene

This was prepared as follows:- A solution of benzyl bromide (10.26 g; 60 mmol) and 4chloro-3-nitrophenol (8.7 g; 50 mmol) in DMF (250 ml) was treated with Na$_2$CO$_3$ (10.6 g; 0.1 mol) and the mixture was stirred at room temperature for 3 days. The mixture was poured into water and extracted with Et$_2$O. The organic phase was washed with brine and dried over MgSO$_4$. The residue was purified by flash chromatography eluting with CH$_2$Cl$_2$ to give 5-benzyloxy-2-chloro-nitrobenzene as a pale yellow solid (12.32 g).

Yield: 94%

$^1$H NMR spectrum (CDCl$_3$): 5.10 (s, 2H); 7.12 (dd, 1H); 7.36–7.43 (m, 6H); 7.47 (d, 1H).

| Elemental analysis: | Found | C 58.72 | H 3.81 | N 5.26 |
|---|---|---|---|---|
| C$_{13}$H$_{10}$ClNO$_3$; 0.1 H$_2$O | Requires | C 58.82 | H 3.87 | N 5.28 |

EXAMPLE 21

6-Benzyloxy-2-(4-methylpiperazin-1-yl-4-oxobutanoylamino)-1H-indole-3-carbonitrile

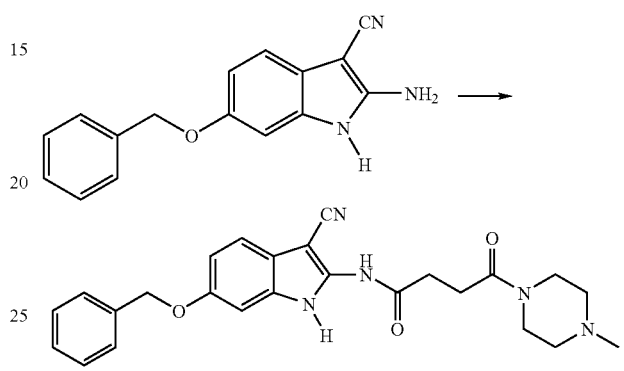

Example 21

Using the general method described for Examples 12 and 13, 6-benzyloxy-2-(4-methylpiperazin-1-yl-4-oxobutanoylamino)-1H-indole-3-carbonitrile (128 mg) was obtained as a white solid from 6-benzyloxy-2-amino-1H-indole-3-carbonitrile (Example 20)(120 mg; 0.46 mmol) after purification by flash chromatography eluting with increasingly polar mixtures of MeOH/CH$_2$Cl$_2$ (3 to 10% MeOH).

Yield: 63%

$^1$H NMR spectrum (DMSO d$_6$): 2.18 (s, 3H); 2.22 (m, 2H); 2.31 (m, 2H); 2.6–2.75 (m, 4H); 3.4–3.5 (m, 4H); 5.08 (s, 2H); 6.68 (dd, 1H); 7.18 (d, 1H); 7.31 (d, 1H); 7.33 (t, 1H); 7.39 (t, 2H); 7.46 (d, 2H); 11.4 (br s, 1H); 11.9 (br s, 1H).

LCMS-ESI: 446 [M+H]$^+$

| Elemental analysis: | Found | C 61.52 | H 6.11 | N 14.03 |
|---|---|---|---|---|
| C$_{25}$H$_{27}$N$_5$O$_3$; 1.1 HCl 0.2 H$_2$O | Requires | C 61.38 | H 5.87 | N 14.31 |

EXAMPLE 22

5-(4-Benzyloxyphenoxy)-2-amino-1H-indole-3-carbonitrile

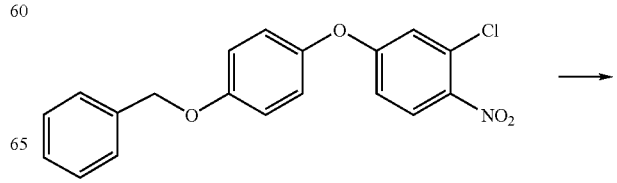

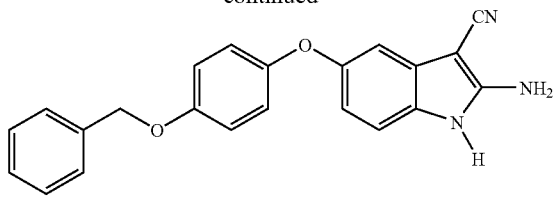

Example 22

Using the general method described in Example 2, except that two equivalents of aqueous NaOH were employed, 5-(4-benzyloxyphenoxy)-2-amino-1H-indole-3-carbonitrile (1.28 g) was obtained as a white solid from 4-(4-benzyloxyphenoxy)-2-chloro-nitrobenzene (2.1 g; 5.9 mmol) after purification by flash chromatography eluting with increasingly polar mixtures of $CH_2Cl_2$/EtOAc (0 to 80% EtOAc).

Yield: 61%

$^1$H NMR spectrum (DMSO $d_6$): 5.07 (s, 2H); 6.58 (dd, 1H); 6.63 (d, 1H); 6.78 (s, 2H); 6.92 (m, 2H); 7.00 (m, 2H); 7.09 (d, 1H); 7.34 (t, 1H); 7.40 (t, 2H); 7.46 (d, 2H); 10.69 (br s, 1H).

LCMS-ESI: 356 [M+1]$^+$ 4-(4-Benzyloxyphenoxy)-2-chloro-nitrobenzene was prepared as follows:

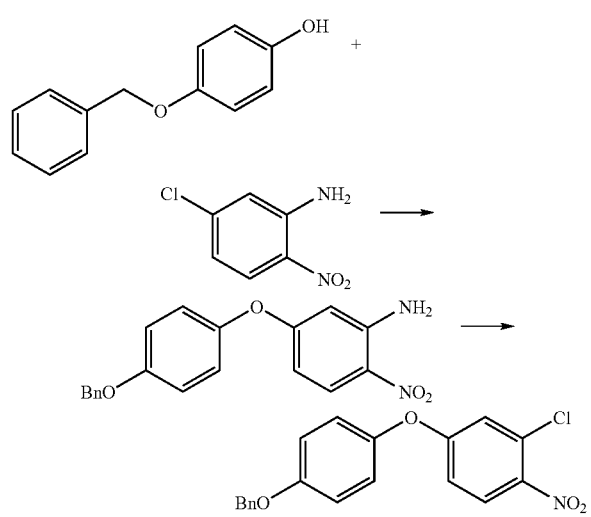

4-(4-Hydroxyphenylsulphanyl)-2-amino-nitrobenzene

Using the general method described for 4-(4-hydroxyphenylsulphanyl)-2-amino-nitrobenzene in Example 2, except that one equivalent of NaH was used, 4-(4-benzyloxyphenoxy)-2-amino-nitrobenzene (5.88 g) was prepared from 4-chloro-2-amino-nitrobenzene (4.30 g; 25 mmol).

Yield: 70%

$^1$H NMR spectrum (CDCl$_3$): 5.11 (s, 2H); 6.25–6.30 (m, 2H); 7.11 (s, 4H); 7.3–7.5 (m, 7H); 7.98 (d, 1H).

MS-ESI: 337 [M+H]$^+$ 4-(4-Benzyloxyphenoxy)-2-chloro-nitrobenzene

Similarly, using the general method described for 4-(4-hydroxyphenylsulphanyl)-2-chloro-nitrobenzene in Example 2, 4-(4-benzyloxyphenoxy)-2-chloro-nitrobenzene (2.09 g) was prepared from 4-(4-benzyloxyphenoxy)-2-amino-nitrobenzene (9.6 g; 28.5 mmol) after purification by flash chromatography eluting with increasingly polar mixtures of EtOAc/$CH_2Cl_2$ (10 to 20% EtOAc).

Yield: 20%

$^1$H NMR spectrum (DMSO $d_6$): 5.13 (s, 2H); 7.01 (dd, 1H); 7.15 (m, 4H); 7.22 (d, 1H); 7.35 (t, 1H); 7.41 (t, 2H); 7.48 (d, 2H); 8.13 (d, 1H).

MS-ESI: 357 [M+H]$^+$

EXAMPLE 23

5-(4-Hydroxyphenoxy)-2-amino-1H-indole-3-carbonitrile

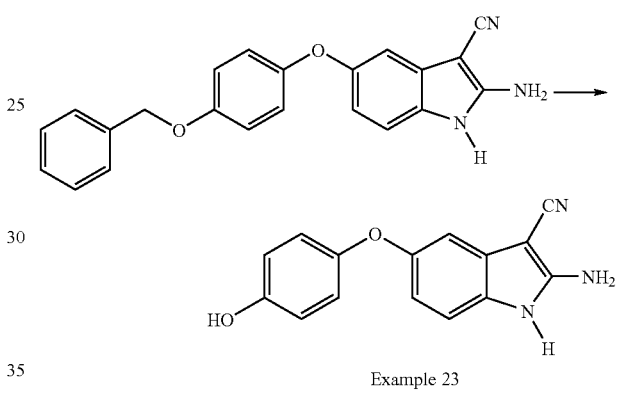

Example 23

Using the general method of hydrogenolysis described in Example 16, 5-(4-hydroxyphenoxy)-2-amino-1H-indole-3-carbonitrile (570 mg) was obtained as a white solid from 5-(4-benzyloxyphenoxy)-2-amino-1H-indole-3-carbonitrile (Example 22) (1.0 g; 2.81 mmol) after purification by flash chromatography eluting with EtOAc.

Yield: 76%

$^1$H NMR spectrum (DMSO $d_6$): 6.54 (dd, 1H); 6.58 (d, 1H); 6.73 (d, 2H); 6.75 (s, 2H); 6.81 (d, 2H); 7.06 (d, 1H) 9.21 (br s, 1H); 10.64 (br s, 1H).

LCMS-ESI: 266 [M+H]$^+$

| Elemental analysis: | Found | C 67.96 | H 4.37 | N 15.73 |
|---|---|---|---|---|
| $C_{15}H_{11}N_3O_2$ | Requires | C 67.92 | H 4.18 | N 15.84 |

EXAMPLE 24

5-[4-(4-Methylpiperazin-1-yl-4-oxobutanoyloxy)phenoxy]-2-amino-1H-indole-3-carbonitrile

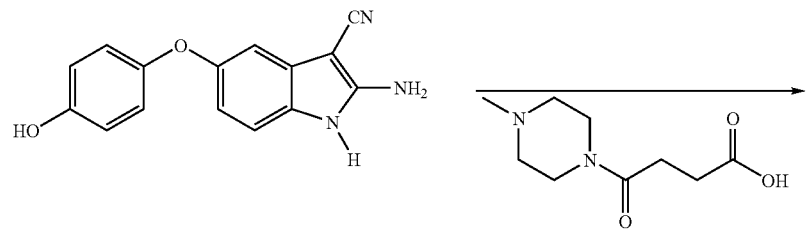

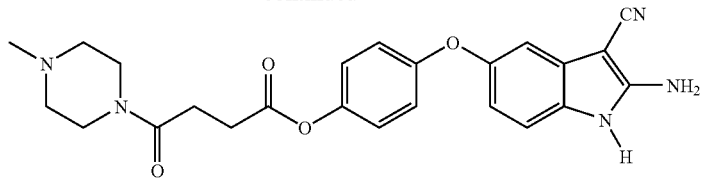

Example 24

A solution of 5-(4-hydroxyphenoxy)-2-amino-1H-indole-3-carbonitrile (Example 23)(130 mg; 0.5 mmol) and 3-(N-methylpiperazin-1-ylcarbonyl)propanoic acid(128 mg 0.63 mmol) in a mixture of $CH_2Cl_2$ (5 ml) and $CH_3CN$ (0.5 ml) was treated at room temperature with EDCI (122 mg; 0.63 mmol) and a catalytic quantity of DMAP (20 mg). The mixture was stirred for overnight and was directly purified by flash chromatography eluting with increasingly polar mixtures of $MeOH/CH_2Cl_2$ (5 to 10% MeOH). The appropriate fractions were evaporated to give 5-[4-(4-methylpiperazin-1-yl-4-oxobutanoyloxy)phenoxy]-2-amino-1H-indole-3-carbonitrile as a white solid (150 mg).

Yield: 67%

$^1$H NMR spectrum (DMSO $d_6$): 2.17 (s, 3H); 2.23 (m, 2H); 2.30 (m, 2H); 2.72 (m, 4H); 3.45 (m, 4H); 6.61 (dd, 1H); 6.73 (d, 1H); 6.82 (s, 2H); 6.94 (d, 2H); 7.04 (d, 2H); 7.13 (d, 1H); 10.73 (s, 1H).

MS-ESI: 448 [M+H]$^+$

| Elemental analysis: | Found | C 62.56 | H 5.98 | N 15.02 |
| --- | --- | --- | --- | --- |
| $C_{24}H_{25}N_5O_4$; 0.8 $H_2O$ | Requires | C 62.41 | H 5.80 | N 15.16 |

EXAMPLE 25

5-(3-Aminobenzyloxy)-2-amino-1-methyl-1H-indole-3-carbonitrile

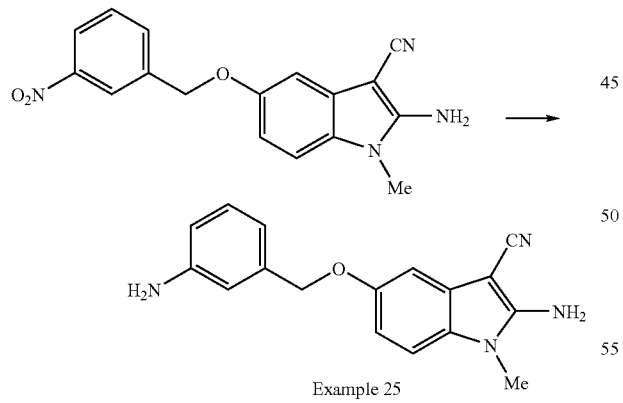

Example 25

A solution of 5-(3-nitrobenzyloxy)-2-amino-1-methyl-1H-indole-3-carbonitrile (40 mg; 0.12 mol) in MeOH (6 ml) was treated with $K_2CO_3$ (6 mg) and hydrogenated over $PtO_2$ (6 mg) at 45 psi at room temperature for 1 hour. After filtration and evaporation to dryness, the residue was purified by flash chromatography eluting with $MeOH/CH_2Cl_2$ (5% MeOH) and the appropriate factions were evaporated to give 5-(3-aminobenzyloxy)-2-amino-1-methyl-1H-indole-3-carbonitrile (32 mg).

Yield: 91%

$^1$H NMR spectrum (DMSO $d_6$): 3.48 (s, 3H); 4.94 (s, 2H); 5.09 (s, 2H); 6.50 (dd, 1H); 6.57 (d, 1H); 6.63 (m, 2H); 6.77 (d, 1H); 6.90 (s, 2H); 7.01 (t, 1H); 7.11 (d, 1H).

LCMS-ESI: 293 [M+H]$^+$

| Elemental analysis: | Found | C 64.10 | H 5.64 | N 16.57 |
| --- | --- | --- | --- | --- |
| $C_{17}H_{16}N_4O$; 0.75 $H_2O$ 0.1 MeOH 0.2 $CH_2Cl_2$ | Requires | C 63.73 | H 5.66 | N 17.18 |

5-(3-Nitrobenzyloxy)-2-amino-1-methyl-1H-indole-3-carbonitrile was prepared as follows:

4-Benzyloxy-2-fluoronitrobenzene

A solution of 3-fluoro-4-nitrophenol (25 g; 0.159 mol) in DMF (600 ml) under argon was treated at room temperature with $Na_2CO_3$ (33.7 g; 0.318 mol). The mixture was stirred and treated dropwise with benzyl bromide (32.6 g; 0.19 mol). Stirring was continued for 3 days when the mixture was poured into water and extracted with $Et_2O$. The organic phase was washed with water, brine and dried over $MgSO_4$.

Evaporation gave 4-benzyloxy-2-fluoronitrobenzene as a yellow solid (38 g).

Yield: 97%

¹H NMR spectrum (CDCl₃): 5.15 (s, 2H); 6.8–6.9 (m, 2H); 7.35–7.5 (m, 5H); 8.1 (t, 1H).

| Elemental analysis: | Found | C 63.25 | H 4.24 | N 5.73 |
|---|---|---|---|---|
| $C_{13}H_{10}FNO_3$ | Requires | C 63.16 | H 4.08 | N 5.67 |

5-Benzyloxy-2-amino-1H-indole-3-carbonitrile

Using the general method described in Example 2, except that two equivalents of aqueous NaOH were employed, 5-benzyloxy-2-amino-1H-indole-3-carbonitrile (31.5 g) was obtained as a pale rose solid from 4-benzyloxy-2-fluoronitrobenzene (38 g; 0.15 mol) after purification by trituration with CH₂Cl₂.

Yield: 80%

¹H NMR spectrum (DMSO d₆): 5.07 (s, 2H); 6.58 (dd, 1H); 6.66 (s, 2H); 6.75 (d, 1H); 7.01 (d, 1H); 7.25–7.5 (m, 5H); 10.51 (s, 1H).

LCMS-ESI: 264 [M+H]⁺

| Elemental analysis: | Found | C 70.91 | H 4.95 | N 15.77 |
|---|---|---|---|---|
| $C_{16}H_{13}N_3O$; 0.4 H₂O | Requires | C 71.04 | H 5.14 | N 15.53 |

5-Benzyloxy-2-amino-1-methyl-1H-indole-3-carbonitrile

A solution of 5-benzyloxy-2-amino-1H-indole-3-carbonitrile (2.96 g; 11.25 mmol) in DMF (20 ml) under argon was treated at room temperature with Cs₂CO₃ (4.4 g; 13.5 mmol). The mixture was stirred and treated dropwise with methyl iodide (0.84 ml; 13.48 mmol). Stirring was continued for 1 hour when the mixture was poured into water. The precipitate was filtered, washed with water and dried to give 5-benzyloxy-2-amino-1-methyl-1H-indole-3-carbonitrile as a beige solid (2.77 g).

Yield: 90%

¹H NMR (DMSO d₆): 3.49 (s, 3H); 5.11 (s, 3H); 6.68 (dd, 1H); 6.82 (d, 1H); 6.91 (s, 2H); 7.13 (d, 1H); 7.35 (t, 1H); 7.41 (m, 2H); 7.47 (d, 2H).

| Elemental analysis: | Found | C 72.95 | H 5.39 | N 15.16 |
|---|---|---|---|---|
| $C_{17}H_{15}N_3O$; 0.2 H₂O | Requires | C 72.68 | H 5.53 | N 14.96 |

5-Hydroxy-2-amino-1-methyl-1H-indole-3-carbonitrile

Using the general method of hydrogenolysis described in Example16, 5-hydroxy-2-amino-1-methyl-1H-indole-3-carbonitrile (1.81 g) was obtained as a white solid from 5-benzyloxy-2-amino-1-methyl-1H-indole-3-carbonitrile (2.6 g; 9.38 mmol) after purification by flash chromatography eluting with EtOAc.

Yield: 100%

¹H NMR spectrum (DMSO d₆): 3.45 (s, 3H); 6.43 (dd, 1H); 6.56 (d, 1H); 6.81 (s, 2H); 6.99 (d, 1H); 8.83 (s, 1H).

LCMS-ESI: 188 [M+H]⁺

| Elemental analysis: | Found | C 64.05 | H 4.92 | N 22.20 |
|---|---|---|---|---|
| $C_{10}H_9N_3O$ | Requires | C 64.16 | H 4.85 | N 22.45 |

5-(3-Nitrobenzyloxy)-2-amino-1-methyl-1H-indole-3-carbonitrile

A solution of 5-hydroxy-2-amino-1-methyl-1H-indole-3-carbonitrile (100 mg; 0.53 mmol) and 3-nitrobenzyl bromide (130 mg; 0.6 mmol) in DMF (5 ml) was treated with Cs₂CO₃ (520 mg; 1.6 mmol) and the mixture was stirred for 2 hours. Water (80 ml) was added and the precipitate was filtered, taken up in methanol, filtered, washed and dried to give 5-(3-nitrobenzyloxy)-2-amino-1-methyl-1H-indole-3-carbonitrile (96 mg).

Yield: 56%

¹H NMR spectrum (DMSO d₆): 3.49 (s, 3H); 5.28 (s, 2H); 6.71 (dd, 1H); 6.85 (d, 1H); 6.94 (s, 2H); 7.15 (d, 1H); 7.72 (t, 1H); 7.94 (d, 1H); 8.20 (d, 1H); 8.33 (s, 1H).

LCMS-ESI: 321 [M−H]⁻

EXAMPLE 26

5-(3-Glycylbenzyloxy)-2-amino-1-methyl-1H-indole-3-carbonitrile

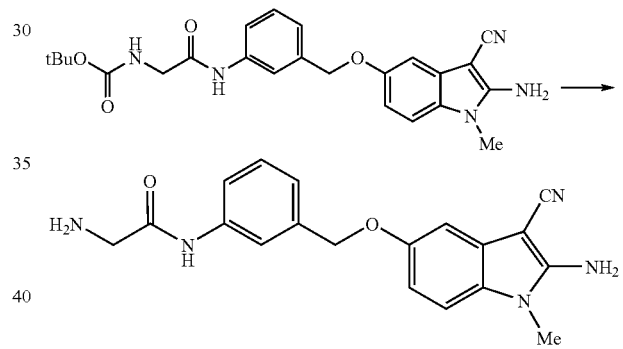

Example 26

A solution of 5-[3-(N-t-butoxycarbonylglycyl)benzyloxy]-2-amino-1-methyl-1H-indole-3-carbonitrile (188 mg; 0.42 mmol) in EtOAc (10 ml) that was saturated with gaseous HCl was stirred at room temperature for 24 hours. An excess of Et₂O was added and the precipitate was filtered and dried to give the hydrochloride of 5-(3-glycylbenzyloxy)-2-amino-1-methyl-1H-indole-3-carbonitrile (170 mg).

Yield: 100%

¹H NMR spectrum (DMSO d₆): 3.47 (s, 3H); 3.80 (s, 2H); 5.10 (s, 2H); 6.65 (dd, 1H); 6.78 (d, 1H); 6.95 (br s, 2H); 7.10 (d, 1H); 7.18 (d, 1H); 7.36 (t, 1H); 7.58 (d, 1H); 7.68 (s, 1H); 8.14 (br s, 3H); 10.54 (s, 1H).

LCMS-ESI : 350 [M+H]⁺

| Elemental analysis: | Found | C 52.53 | H 5.58 | N 15.53 |
|---|---|---|---|---|
| $C_{19}H_{19}N_5O_2$ ; 0.8 H₂O 0.3 EtOAc 1.9 HCl | Requires | C 52.80 | H 5.46 | N 15.24 |

5-[3-(N-t-Butyloxycarbonylglycyl)benzyloxyl-2-amino-1-methyl-1H-indole-3-carbonitrile 5-[3-(N-t-Butoxycarbonylglycyl)benzyloxy]-2-amino-1-methyl-1H-indole-3-carbonitrile (188 mg) was prepared using the general coupling method described in Example 16

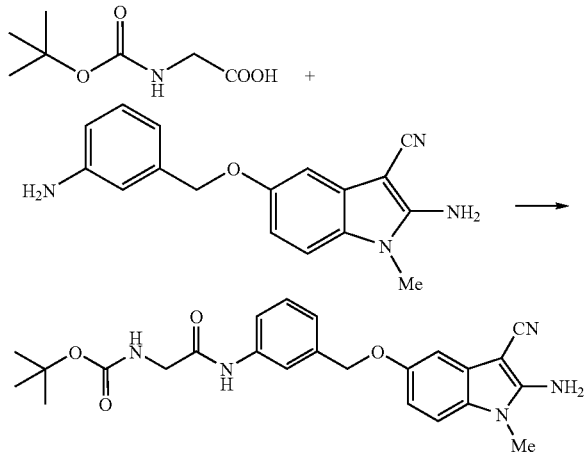

as a white solid from 5-(3-aminobenzyloxy)-2-amino-1-methyl-1H-indole-3-carbonitrile (150 mg; 0.51 mmol) after purification by flash chromatography eluting with EtOAc/CH$_2$Cl$_2$ (50/50).

Yield: 80%

$^1$H NMR spectrum (DMSO d$_6$): 1.42 (s, 9H); 3.50 (s, 3H); 3.74 (d, 2H); 5.09 (s, 2H); 6.67 (dd, 1H); 6.82 (d, 1H); 6.92 (s, 2H); 7.05 (t, 1H); 7.14 (m, 2H); 7.33 (t, 1H); 7.58 (d, 1H); 7.69 (s, 1H); 9.97 (s, 1H).

LCMS-ESI: 450 [M+H]$^+$

EXAMPLE 27

5-(3-Serylbenzyloxy)-2-amino-1-methyl-1H-indole-3-carbonitrile

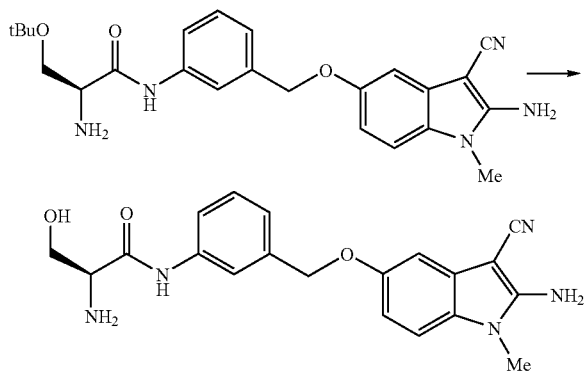

Example 27

Using the general method of deprotection described in Example 18, 5-(3-serylbenzyloxy)-2-amino-1H-indole-3-carbonitrile (177 mg) was obtained as its hydrochloride as a glassy solid from 5-[3-(O-t-butylseryl)benzyloxy]-2-amino-1-methyl-1H-indole-3-carbonitrile (280 mg; 0.64 mmol) after purification by reverse phase C18 preparative HPLC eluting with MeOH/H$_2$O/HCl (80/19/1)

Yield: 70%

$^1$H NMR spectrum (DMSO d$_6$): 3.49 (s, 3H); 3.7 (s, 1H); 3.87 (d, 2H); 4.04 (m, 1H); 5.11 (s, 2H); 6.66 (dd, 1H); 6.80 (d, 1H); 6.95 (br s, 2H); 7.12 (d, 1H); 7.20 (d, 1H); 7.38 (t, 1H); 7.62 (d, 1H); 7.75 (s, 1H); 8.30 (m, 3H); 10.67 (s, 1H).

LCMS-ESI: 380 [M+H]$^+$

| Elemental analysis: | Found | C 51.84 | H 5.51 | N 14.72 |
|---|---|---|---|---|
| C$_{20}$H$_{21}$N$_5$O$_3$; 1.4 HCl 1.8 H$_2$O | Requires | C 51.69 | H 5.65 | N 15.07 |

5-[3-(O-t-Butyl-N-FMOC-seryl)benzyloxyl]-2-amino-1-methyl-1H-indole-3-carbonitrile This was prepared using the general coupling method described in Example 16, 5-[3-(O-t-butyl-N-FMOC-seryl)benzyloxy]-2-amino-1-methyl-1H-indole-3-carbonitrile (730 mg) was obtained as a white solid from 5-(3-aminobenzyloxy)-2-amino-1-methyl-1H-indole-3-carbonitrile (Example 25)(700 mg; 2.38 mmol) after purification by flash chromatography eluting with EtOAc/CH$_2$Cl$_2$ (20% EtOAc).

Yield: 64%

$^1$H NMR spectrum (DMSO d$_6$): 1.13 (s, 9H); 3.48 (s, 3H); 3.55 (m, 2H); 4.2–4.35 (m, 4H); 5.09 (s, 2H); 6.66 (dd, 1H); 6.81 (d, 1H); 6.92 (s, 2H); 7.13 (m, 2H); 7.33 (m, 3H); 7.43 (m, 2H); 7.56 (m, 2H); 7.76 (m, 3H); 7.90 (d, 2H); 10.06 (s, 1H).

5-[3-(O-t-Butylseryl)benzyloxy]-2-amino-1-methyl-1H-indole-3-carbonitrile

Using the general FMOC deprotection method described in Example 16, 5-[3-(O-t-butylseryl)benzyloxy]-2-amino-1-methyl-1H-indole-3-carbonitrile (280 mg) was obtained as a white solid from 5-[3-(O-t-butyl-N-FMOC-seryl)benzyloxy]-2-amino-1-methyl-1H-indole-3-carbonitrile (730 mg; 1.52 mmol) after purification by flash chromatography eluting with increasingly polar mixtures of MeOH/CH$_2$Cl$_2$ (2 to 5% MeOH).

Yield: 42%

$^1$H NMR spectrum (DMSO d$_6$): 1.13 (s, 9H); 1.93 (br s, 2H); 3.4–3.5 (m, 3H); 3.48 (s, 15 3H); 5.08 (s, 2H); 6.66 (dd, 1H); 6.80 (d, 1H); 6.91 (s, 2H); 7.13 (m, 2H); 7.32 (t, 1H); 7.61 (d, 1H); 7.76 (s, 1H) 9.88 (br s, 1H).

MS-ESI: 436 [M+H]$^+$

EXAMPLE 28

5-(4-Hydroxyphenoxy)-2-amino-1-methyl-1H-indole-3-carbonitrile

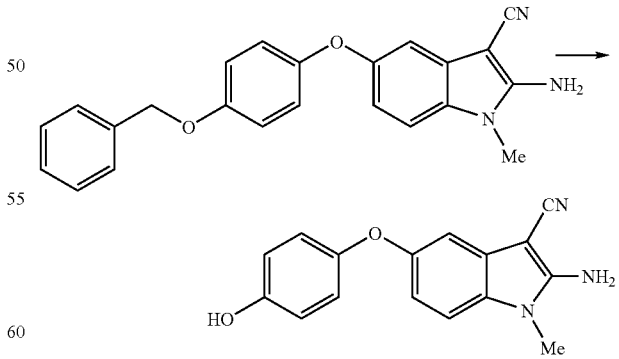

Example 28

Using the general method of hydrogenolysis described in Example 16 at 18 psi for 15 minutes, 5-(4-hydroxyphenoxy)-2-amino-1-methyl-1H-indole-3- carbonitrile (1.45 g) was obtained as a white solid from 5-(4-benzyloxyphenoxy)-2-amino-1-methyl-1H-indole-3-carbonitrile (2.02 g; 5.47 mmol) after purification by flash chromatography eluting with MeOH/CH$_2$Cl$_2$ (10% MeOH).

Yield: 95%

$^1$H NMR spectrum (DMSO d$_6$): 3.49 (s, 3H); 6.60 (dd, 1H); 6.61 (d, 1H); 6.74 (d, 2H); 6.82 (d, 2H); 6.99 (s, 2H); 7.16 (d, 1H); 9.22 (s, 1H).

LCMS-ESI: 280 [M+H]$^+$ 5-(4-benzyloxyphenoxy)-2-amino-1-methyl-1H-indole-3-carbonitrile This was prepared using the general method of selective N-alkylation described for 5-benzyloxy-1H-indole-3-carbonitrile in Example 25, 5-(4-benzyloxyphenoxy)-2-amino-1-methyl-1H-indole-3-carbonitrile (1.77 g) was obtained as a white solid from 5-(4-benzyloxyphenloxy)-2-amino-1H-indole-3-carbonitrile (2.0 g; 5.63 mmol) after purification by flash chromatography eluting with increasingly polar mixtures of CH$_2$Cl$_2$/EtOAc (10 to 20% EtOAc).

Yield: 85%

$^1$H NMR spectrum (DMSO d$_6$): 3.50 (s, 3H); 5.07 (s, 2H); 6.65 (dd, 1H); 6.66 (d, 1H); 6.93 (d, 2H); 7.00 (d, 2H); 7.01 (s, 2H); 7.19 (d, 1H); 7.33 (t, 1H); 7.40 (t, 2H); 7.45 (d, 2H).

EXAMPLE 29

5-(4-Phosponooxyphenoxy)-2-amino-1-methyl-1H-indole-3-carbonitrile

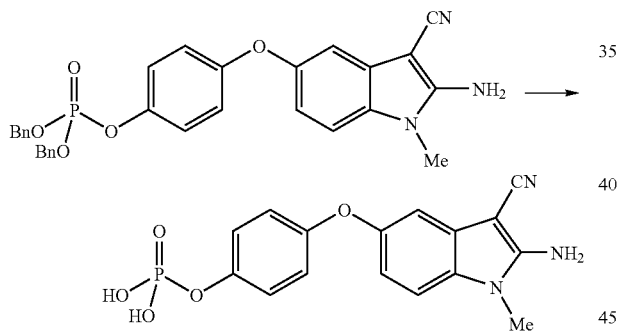

Example 29

Using the general method of hydrogenolysis described in Example 16 at 10 psi for 1hour, 5-(4-phosponooxyphenoxy)-2-amino-1-methyl-1H-indole-3-carbonitrile (920 mg) was obtained as a white solid from 5-[4-(O,O-dibenzylphosponooxy)phenoxy]-2-amino-1-methyl-1H-indole-3-carbonitrile (1.71 g; 3.16 mmol) after purification by HP20SS chromatography eluting with MeOH/H$_2$O (0 to 100% MeOH).

Yield: 80%

A small sample (300 mg) was repurified by reverse phase C18 preparative HPLC eluting with MeOH/H$_2$O/AcOH (80/19/1) to give pure 5-(4-phosponooxyphenoxy)-2-amino-1-methyl-1H-indole-3-carbonitrile (150 mg).

$^1$H NMR spectrum (DMSO d$_6$+TFA): 3.49 (s, 3H); 6.69 (dd, 1H); 6.76 (d, 1H); 6.95 (d, 2H); 7.15 (d, 2H); 7.23 (d, 1H); 12.37 (br s, 2H); 12.64 (br s, 2H).

LCMS-ESI: 360 [M+H]$^+$

| Elemental analysis: | Found | C 51.45 | H 3.96 | N 11.12 |
|---|---|---|---|---|
| C$_{16}$H$_{14}$N$_3$O$_5$P; 0.77 H$_2$O | Requires | C 51.50 | H 4.20 | N 11.26 |

5-[4-(O,O-Dibenzylphosponooxy)phenoxy]-2-amino-1-methyl-1H-indole-3-carbonitrile This was prepared as follows: A solution of 5-(4-hydroxyphenoxy)-2-amino-1-methyl-1H-indole-3-carbonitrile (1.4 g; 5 mmol) in acetonitrile (80 ml), CCl$_4$ (2.44 ml; 25 mmol) and diisopropylethylamine (1.82 ml; 10.5 mmol) was treated with a catalytic amount of DMAP (50 mg) and then cooled to 0° C. Dibenzyl phosphite (1.7 ml; 7.51 mmol) was added and the temperature allowed to rise to room temperature over 30 minutes. The mixture was treated with aqueous KH$_2$PO$_4$ (0.5 M), the acetonitrile evaporated and the mixture extracted with Et$_2$O. The organic phase was washed with water, brine and dried over MgSO$_4$. The residue was purified by flash chromatography eluting with increasingly polar mixtures of CH$_2$Cl$_2$/EtOAc (10 to 20% EtOAc) to give 5-[4-(O,O-dibenzylphosponooxy)phenoxy]-2-amino-1-methyl-1H-indole-3-carbonitrile (1.76 g).

Yield: 65%

$^1$H NMR spectrum (CDCl$_3$): 3.52 (s, 3H); 5.15 (d, 4H); 6.68 (dd, 1H); 6.76 (d, 1H); 6.91 (d, 2H); 7.06 (s, 2H); 7.13 (d, 2H); 7.23 (d, 1H); 7.36 (m, 10H).

EXAMPLE 30

5-Benzyloxy-1-carbamoylmethy-2-amino-1H-indole-3-carbonitrile

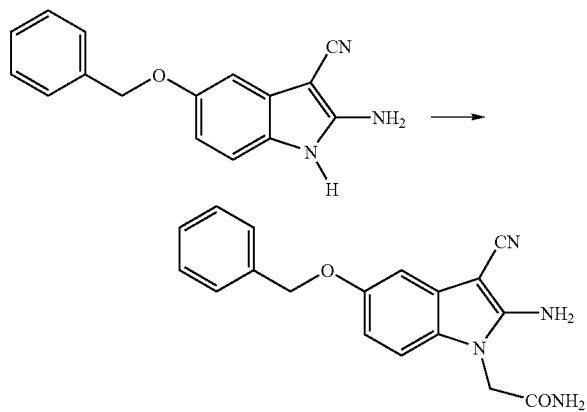

Example 30

Using the general method of selective N-alkylation described for 5-benzyloxy-2-amino-1-methyl-1H-indole-3-carbonitrile in Example 25, using iodoacetamide (222 mg; 1.2 mmol), 5-benzyloxy-1-carbamoylmethyl-2-amino-1H-indole-3-carbonitrile (163 mg) was obtained as a white solid from 5-benzyloxy-2-amino-1H-indole-3-carbonitrile (263 mg; 1.0 mmol) after trituration with Et$_2$O/CH$_2$Cl$_2$.

Yield: 51%

$^1$H NMR spectrum (DMSO d$_6$): 4.61 (s, 2H); 5.11 (s, 2H); 6.65 (dd, 1H); 6.81 (d, 1H); 6.91 (s, 2H); 6.94 (d, 1H); 7.30 (s, 1H); 7.34 (d, 1H); 7.40 (m, 2H); 7.47 (m, 2H); 7.57 (s, 1H).

LCMS-ESI: 319 [M−H]$^-$

| Elemental analysis: | Found | C 65.65 | H 5.01 | N 17.41 |
| $C_{18}H_{16}N_4O_2$ ; 0.45 $H_2O$ | Requires | C 65.82 | H 5.19 | N 17.06 |

EXAMPLE 31

5-(3,5-Dimethoxy-4-hydroxy-phenoxy)-2-amino-1H-indole-3-carbonitrile

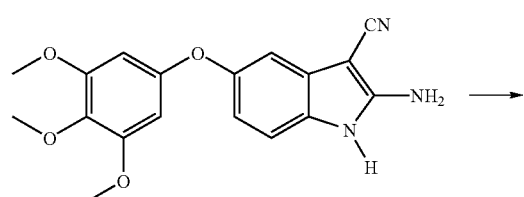
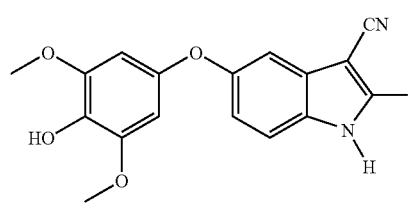

Example 31

A solution of 5-(3,4,5-trimethoxyphenoxy)-2-amino-1H-indole-3-carbonitrile (Example 11) (50 mg; 0.147 mmol) in $CH_2Cl_2$ (1.0 ml) was treated with trimethyl silyl iodide (30 ul; 0.2 mmol) and the mixture was stirred at room temperature overnight. The mixture was treated with aqueous $Na_2S_2O_3$ (0.5 M), the $CH_2Cl_2$ evaporated and the mixture extracted with EtOAc. The organic phase was washed with water, brine and dried over $MgSO_4$. Evaporation gave 5-(3,5-dimethoxy-4-hydroxy-phenoxy)-2-amino-1H-indole-3-carbonitrile (50 mg).

Yield: 100%

$^1$H NMR spectrum (DMSO $d_6$): 3.66 (s, 6H); 6.26 (s, 2H); 6.55 (dd, 1H); 6.62 (d, 1H); 6.74 (s, 2H); 7.05 (d, 1H); 8.04 (s, 1H); 10.62 (s, 1H).

LCMS-ESI: 326 [M+H]$^+$

EXAMPLE 32

5-(3,4,5-Trimethoxyphenoxy)-2-amino-1-methyl-1H-indole-3-carbonitrile

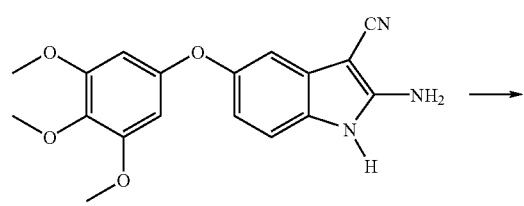

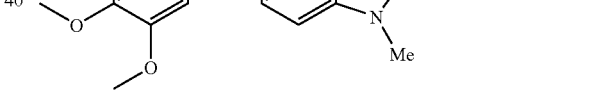

Example 32

Using the general method of selective N-alkylation described in Example 25, 5-(3,4,5-trimethoxyphenoxy)-2-amino-1-methyl-1H-indole-3-carbonitrile (77 mg) was obtained as a white solid from 5-(3,4,5-trimethoxyphenoxy)-2-amino-1H-indole-3-carbonitrile (Example 11) (100 mg; 0.29 mmol) after purification by flash chromatography eluting with $CH_2Cl_2$/EtOAc (10% EtOAc).

Yield: 75%

$^1$H NMR spectrum (DMSO $d_6$): 3.52 (s, 3H); 3.64 (s, 3H); 3.69 (s, 6H); 6.28 (s, 2H); 6.70 (dd, 1H); 6.78 (d, 1H); 7.05 (s, 2H); 7.22 (d, 1H).

LCMS-ESI: 354 [M+H]$^+$

| Elemental analysis: | Found | C 64.69 | H 5.60 | N 11.72 |
| $C_{19}H_{19}N_3O_4$ | Requires | C 64.58 | H 5.42 | N 11.89 |

EXAMPLE 33

5-(3,5-Dimethoxy-4-hydroxy-phenoxy)-2-amino-1-methyl-1H-indole-3-carbonitrile

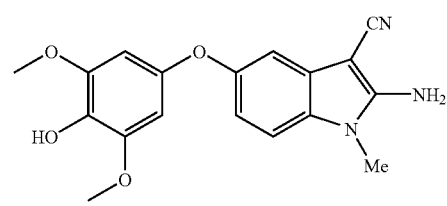

Example 33

Using the general method of selective demethylation described for Example 31, 5-(3,5-dimethoxy-4-hydroxy-phenoxy)-2-amino-1-methyl-1H-indole-3-carbonitrile (50 mg) was obtained as a white solid from 5-(3,4,5-trimethoxyphenoxy)-2-amino-1-methyl-1H-indole-3-carbonitrile (Example 32) (160 mg; 0.45 mmol) after purification by flash chromatography eluting with $CH_2Cl_2$/EtOAc (20% EtOAc).

Yield: 33%

$^1$H NMR spectrum (DMSO $d_6$): 3.51 (s, 3H); 3.69 (s, 6H); 6.30 (s, 2H); 6.66 (dd, 1H); 6.71 (d, 1H); 7.01 (s, 2H); 7.19 (d, 1H); 8.10 (s, 1H).

LCMS-ESI: 340 [M+H]$^+$

| Elemental analysis: | Found | C 63.60 | H 5.27 | N 12.00 |
| --- | --- | --- | --- | --- |
| $C_{18}H_{17}N_3O_4$ | Requires | C 63.71 | H 5.05 | N 12.38 |

EXAMPLE 34

5-(3,4,5-Trimethoxyphenoxy)-2-amino-1-carbamoylmethyl-1H-indole-3-carbonitrile

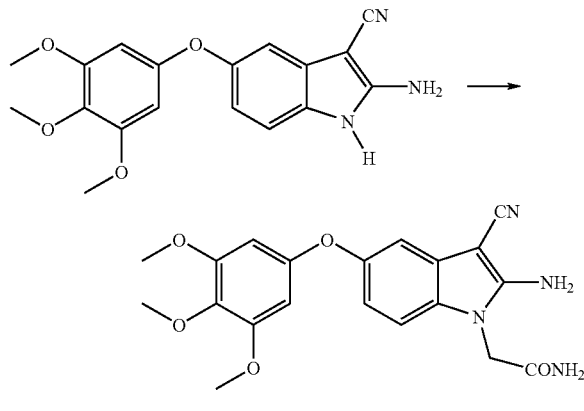

Example 34

Using the general method of selective N-alkylation described for 5-benzyoxy-2-amino-1-methyl-1H-indole-3-carbonitrile in Example 25 using iodoacetamide (350 mg; 1.88 mmol), 5-(3,4,5-trimethoxyphenoxy)-2-amino-1-carbamoylmethyl-1H-indole-3-carbonitrile (192 mg) was obtained as a white solid from 5-(3,4,5-trimethoxyphenoxy)-2-amino-1H-indole-3-carbonitrile (Example 11)(320 mg; 0.94 mmol) after trituration with $Et_2O/CH_2Cl_2$.

Yield: 52%

$^1$H NMR spectrum (DMSO $d_6$): 3.64 (s, 3H); 3.70 (s, 6H); 4.66 (s, 2H); 6.31 (s, 2H); 6.68 (dd, 1H); 6.77 (d, 1H); 7.03 (d, 1H); 7.04 (s, 2H); 7.33 (s, 1H); 7.62 (s, 1H).

LCMS-ESI: 397 [M+H]$^+$

| Elemental analysis: | Found | C 54.81 | H 4.68 | N 12.63 |
| --- | --- | --- | --- | --- |
| $C_{20}H_{20}N_4O_5$ ; 0.8 $H_2O$ 0.45 $CH_2Cl_2$ | Requires | C 54.70 | H 5.05 | N 12.48 |

EXAMPLE 35

5-(3,5-Dimethoxy-4-hydroxyphenoxy)-2-amino-1-carbamoylmethyl-1H-indole-3-carbonitrile

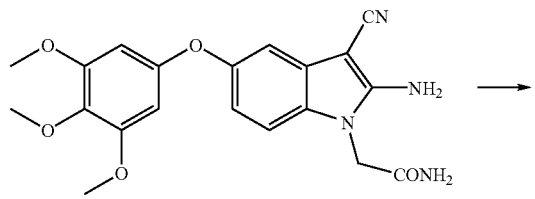

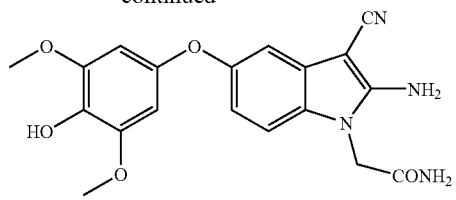

Example 35

Using the general method of selective demethylation described for Example 31 5-(3,5-dimethoxy-4-hydroxyphenoxy)-2-amino-1-carbamoylmethyl-1H-indole-3-carbonitrile (95 mg) was obtained as a beige solid from 5-(3,4,5-trimethoxyphenoxy)-2-amino-1-carbamoylmethyl-1H-indole-3-carbonitrile (150 mg; 0.37 mmol) after trituration with $Et_2O$.

Yield: 67%

$^1$H NMR spectrum (DMSO $d_6$): 3.70 (s, 6H); 4.64 (s, 2H); 6.32 (s, 2H); 6.63 (dd, 1H); 6.69 (d, 1H); 7.00 (d, 1H); 7.01 (s, 2H); 7.32 (s, 1H); 7.61 (s, 1H); 8.11 (s, 1H).

LCMS-ESI: 383 [M+H]$^+$

EXAMPLE 36

5-(3,5-Dimetboxy-4-phosphonooxyphenoxy)-2-amino-1-methyl-1H-indole-3-carbonitrile

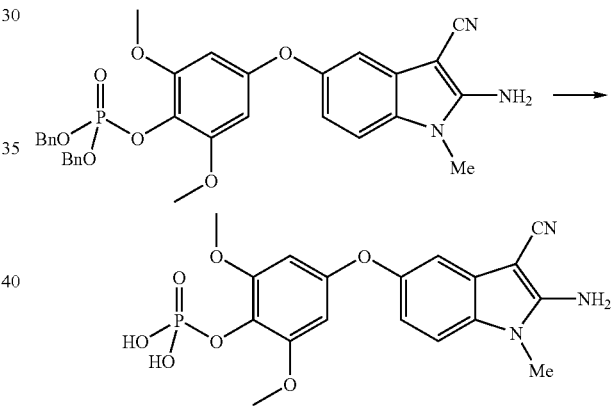

Example 36

Using the general method of hydrogenolysis described in Example 16 at 2 psi for 2 hours, 5-(3,5-dimethoxy-4-phosphonooxyphenoxy)-2-amino-1-methyl-1H-indole-3-carbonitrile (37 mg) was obtained as a white solid from 5-[3,5-dimethoxy-4-(O,O-dibenzylphosphonooxy)phenoxy]-2-amino-1-methyl-1H-indole-3-carbonitrile (88 mg; 0.14 mmol) after purification by HP20SS chromatography eluting with increasingly polar mixtures of MeOH/$H_2O$ (0 to 50% MeOH).

Yield: 60%

$^1$H NMR spectrum (DMSO $d_6$): 3.49 (s, 3H); 3.62 (s, 6H); 6.20 (s, 2H); 6.68 (dd, 1H); 6.78 (d, 1H); 7.01 (s, 2H); 7.23 (d, 1H).

| Elemental analysis: | Found | C 41.45 | H 4.11 | N 7.69 |
| --- | --- | --- | --- | --- |
| $C_{18}H_{16}N_3O_7P$; 2.7 $H_2O$ 2.3 Na | Requires | C 41.67 | H 4.16 | N 8.10 |

5-[3,5-Dimethoxy-4-(O,O-dibenzylphosphonooxy) phenoxy]-2-amino-1-methyl-1H-indole-3-carbonitrile Using the general method of phosphorylation described in Example 29, 5-[3,5-dimethoxy-4-(O,O-dibenzylphosphonooxy)phenoxy]-2-amino-1-methyl-1H-indole-3-carbonitrile (88 mg) was obtained as a white solid from 5-(3,5-dimethoxy-4-hydroxy-phenoxy)-2-amino-1-methyl-1H-indole-3-carbonitrile (114 mg; 0.33 mmol) after purification by flash chromatography eluting with $CH_2Cl_2$/EtOAc(20% EtOAc).

Yield: 44%

$^1$H NMR spectrum (DMSO $d_6$): 3.54 (s, 3H); 3.69 (s, 6H); 5.22 (d, 4H); 6.36 (s, 2H); 6.74 (dd, 1H); 6.83 (d, 1H); 7.07 (s, 2H); 7.26 (d, 1H); 7.3–7.5 (m, 10H).

LCMS-ESI: 599 [M–H]$^-$

What is claimed is:

1. A compound of Formula (I):

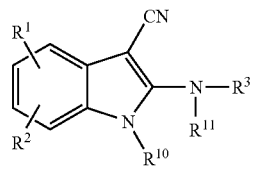

Formula (I)

wherein $R^1$ is a group of Formula (II):

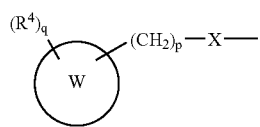

Formula (II)

wherein W is an aryl or a heterocyclic group;

$R^4$ is independently selected from —OH, amino, —OPO$_3$H$_2$, and a lower alkanoylamino group, wherein the amino group is optionally substituted by an amino acid residue and the hydroxy group is optionally esterified;

X is selected from —S—, —O—, —S(O)—, —S(O$_2$)—, and —NH—;

p is an integer from 0 to 4; and q is an integer from 1 to 4;

$R^2$ is selected from hydrogen, halogen, and a lower alkyl group;

$R^3$ and $R^{10}$ are independently selected from hydrogen, lower alkyl, and a group of Formula (IV):

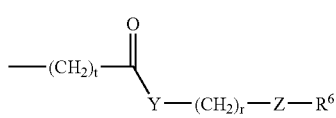

Formula (IV)

wherein Y is selected from —NH—, —O—, and a bond;

Z is selected from —NH—, —O—, —C(O)—, and a bond;

r is an integer from 0 to 4;

t is an integer from 0 to 1;

$R^6$ is hydrogen, lower alkyl, a lower alkoxy group, an aryl group, a heterocyclic group or a group of Formula (V), wherein the aryl group and heterocyclic group are optionally substituted by lower alkyl or a lower alkanoyl group:

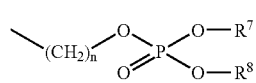

Formula (V)

wherein n is an integer of from 1 to 6;

$R^7$ and $R^8$ are independently selected from hydrogen and an alkaryl group; and $R^{11}$ is hydrogen or lower alkyl;

or a pharmaceutically acceptable salt, or solvate thereof.

2. A compound according to claim 1, or a pharmaceutically acceptable salt, or solvate thereof, wherein X is selected from —S—, —O—, —S(O$_2$)—, and —NH—.

3. A compound according to claim 1 or a pharmaceutically acceptable salt, or solvate thereof, wherein q is 1 and $R^4$ is selected from —OH, amino, —OPO$_3$H$_2$, acetylamino, serylamino, glutamylamino, glycylamino, alanylamino and 4-methylpiperazin-1-ylcarbonylpropanoyloxy.

4. A compound according to claim 1 or a pharmaceutically acceptable salt, or solvate thereof, wherein q is 2 or 3 and $R^4$ is independently selected from —OH and —OPO$_3$H$_2$.

5. A compound according to claim 1 or a pharmaceutically acceptable salt, or solvate thereof, wherein $R^3$ is hydrogen and $R^{10}$ is independently selected from hydrogen and lower alkyl.

6. A compound according to claim 1, selected from 5-(4hydroxyphenylsulphanyl)-2-amino-1H-indole-3-carbonitrile;

5-(4-(methylpiperazin-1-yl-4-oxobutanoyloxy)phenoxy]-2-amino-1H-indole-3-carbonitrile;

5-(4-glycylaminophenoxy)-2-amino-1H-indole-3-carbonitrile;

5-(4-alanylaminophenoxy)-2-amino-1H-indole-3-carbonitrile;

5-(4-α-glutamylaminophenoxy)-2-amino-1H-indole-3-carbonitrile;

5-(3-glycylbenzyloxy)-2-amino-1H-indole-carbonitrile;

5-(4-hydroxyphenoxy)-2-amino-1H-indole-3-carbonitrile;

5-(4-phosphonooxyphenoxy)-2-amino-1H-indole-3-carbonitrile;

5-(3-serylbenzyloxy)-2-amino-1H-indole-3-carbonitrile;

5-(4-acetylaminophenoxy)-2-amino-1H-indole-3-carbonitrile; and 5-(4-serylaminophenoxy)-2-amino-1H-indole-3-carbonitrile;

or a pharmaceutically acceptable salt, or solvate thereof.

7. A compound according to claim 1, which is:

5-(4-aminophenoxy)-2-amino-1H-indole-3-carbonitrile;

or a pharmaceutically acceptable salt, or solvate thereof.

8. A pharmaceutical composition, comprising a pharmaceutically acceptable carrier and a compound of claim 1 or a pharmaceutically acceptable salt or in vivo hydrolysable ester thereof.

9. A compound of Formula (I):

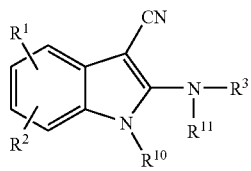

Formula (I)

wherein:

R¹ is a group of Formula (II):

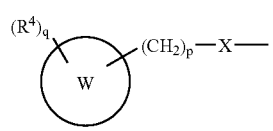

Formula (II)

wherein W is aryl or a heterocyclic group,
R⁴ is independently selected from hydrogen, fluoro, —OH, amino, —OPO₃H₂, a lower alkanoylamino group, and a lower alkoxy group, wherein the amino group is optionally substituted by an amino acid residue and the hydroxy group is optionally esterified;
X is selected from —S(O)—, —S(O₂)— and —Nh—;
p is an integer from 0 to 4; and
q is an integer from 1 to 4;
R² is selected from: hydrogen, halogen and a lower alkyl group;
R³ and R¹⁰ are independently selected from hydrogen, lower alkyl and a group of Formula (IV):

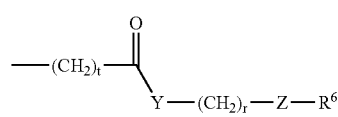

Formula (IV)

wherein Y is selected from —NH—, —O— and a bond;
Z is selected from —NH—, —O—, —C(O)— and a bond;
r is an integer from 0 to 4;
t is an integer from 0 to 1;
R⁶ is hydrogen, lower alkyl, a lower alkoxy group, an aryl group, a heterocyclic group or a group of Formula (V), wherein the aryl group and heterocyclic group are optionally substituted by lower alkyl or a lower alkanoyl group:

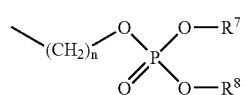

Formula (V)

wherein n is an integer of from 1 to 6, and;
R⁷ and R⁸ are independently selected from hydrogen and an alkaryl group; and
R¹¹ is hydrogen or lower alkyl;
or a salt or solvate thereof.

10. A compound of Formula (I):

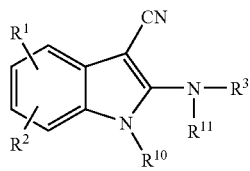

Formula (I)

wherein:

R¹ is a group of Formula (II):

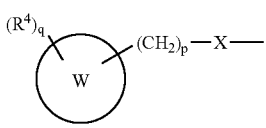

Formula (II)

wherein W is aryl or a heterocyclic group,
R⁴ is independently selected from hydrogen, fluoro, —OH, amino, —OPO₃H₂, a lower alkanoylamino group, and a lower alkoxy group, wherein the amino group is optionally substituted by an amino acid residue and the hydroxy group is optionally esterified;
X is selected from —S(O)—, —S(O₂)— and —NH—;
p is an integer from 0 to 4; and
q is an integer from 1 to 4;
R² is selected from: hydrogen, halogen and a lower alkyl group;
R³ is a lower alkyl or a group of Formula (IV);

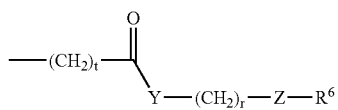

Formula (IV)

wherein Y is selected from —NH—, —O— or a bond;
Z is selected from —NH—, —O—, —C(O)— or a bond;
r is an integer from 0 to 4;
t is an integer from 0 to 1;
R⁶ is hydrogen, an aryl group, a heterocyclic group or a group of Formula (V), wherein the aryl group and heterocyclic group are optionally substituted by lower alkyl or a lower alkanoyl group:

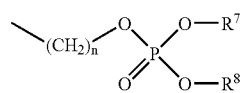

Formula (V)

wherein n is an integer of from 1 to 6, and;
R⁷ and R⁸ are independently selected from hydrogen and an alkaryl group; and
R¹⁰ is hydrogen, lower alkyl or lower carbarnoylalkyl group;
R¹¹ is hydrogen or lower alkyl;
or a salt or solvate thereof.

* * * * *